US009796773B2

(12) United States Patent
Pinter

(10) Patent No.: US 9,796,773 B2
(45) Date of Patent: Oct. 24, 2017

(54) NEUTRALIZING ANTIBODIES THAT BIND TO THE HIV-1 ENV V2 CRITICAL NEUTRALIZATION DOMAIN

(71) Applicant: Rutgers, The State University of New Jersey, New Brunswick, NJ (US)

(72) Inventor: Abraham Pinter, Brooklyn, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 99 days.

(21) Appl. No.: 14/463,040

(22) Filed: Aug. 19, 2014

(65) Prior Publication Data

US 2015/0175679 A1 Jun. 25, 2015

Related U.S. Application Data

(62) Division of application No. 12/309,256, filed as application No. PCT/US2007/015703 on Jul. 10, 2007, now abandoned.

(60) Provisional application No. 60/830,044, filed on Jul. 10, 2006.

(51) Int. Cl.
*C07K 16/10* (2006.01)
*C07K 14/005* (2006.01)
*C12N 7/00* (2006.01)

(52) U.S. Cl.
CPC ........ *C07K 16/1063* (2013.01); *C07K 14/005* (2013.01); *C12N 7/00* (2013.01); *C07K 2317/76* (2013.01); *C12N 2740/16063* (2013.01); *C12N 2740/16122* (2013.01)

(58) Field of Classification Search
CPC .................. C07K 16/1063; C12N 2740/16122
See application file for complete search history.

(56) References Cited

U.S. PATENT DOCUMENTS 6,815,201 B2  11/2004  Pinter ........................ 435/339.1

OTHER PUBLICATIONS

Pinter, A., et al., Jun. 2005, The C108g epitope in the V2 domain of gp120 functions as a potent neutralization target when introduced into envelope proteins derived from human immunodeficiency virus type 1 primary isolates, J. Virol. 79(11):6909-6917.*
Ivanoff, L. A., et al., 1991, Alteration of HIV-1 infectivity and neutralization by a single amino acid replacement in the V3 loop domain, AIDS Res. Human Retrovir. 7(7):595-603.*
Fung, M. S. C., et al., 1992, Identification and characterization of a neutralization site within the second variable region of human immunodeficiency virus type 1 gp120, J. Virol. 66(2):848-856.*
McKeating, J. A., et al., 1993, Characterization of neutralizing monoclonal antibodies to linear and conformation-dependent epitopes within the first and second variable domains of human immunodeficiency virus type 1 gp120, J. Virol. 67(8):4932-4944.*
Pinter, A., et al., 2005, The C108g epitope in the V2 domain of gp120 functions as a potent neutralization target when introduced into envelope proteins derived from human immunodeficiency virus type 1 primary isolates, J. Virol. 79(11):6909-6917.*
Gorny, M. K., et al., 2005, Identification of a new quaternary neutralizing epitope on human immunodeficiency virus type 1 virus particles, J. Virol. 79(8):5232-5237.*
Burton et al. "HIV Vaccine Design and the Neutralizing Antibody Problem" Nature Immunology 2004 5(3):223-236.
Gorny et al. "Human Anti-V2 Monoclonal Antibody That Neutralizes Primary but Not Laboratory Isolates of Human Immunodeficiency Virus Type 1" Journal of Virology 1994 68(12):8312-8320.
Gorny et al. "Identification of a New Quaternary Neutralizing Epitope on Human Immunodeficiency Virus Type 1 Virus Particles" Journal of Virology 2005 79(8):5232-5237.
Haynes et al. "Cardiolipin Polyspecific Autoreactivity in Two Broadly Neutralizing HIV-1 Antibodies" Science 2005 308(5730):1906-1908.
Kunert et al. "Characterization of Molecular Features, Antigen-Binding, and in Vitro Properties of IgG and IgM Variants of 4E10, an Anti-HIV Type 1 Neutralizing Monoclonal Antibody" AIDS Research and Human Retroviruses 2004 20(7):755-762.
McKeating et al. "Characterization of Neutralizing Monoclonal Antibodies to Linear and Conformation-Dependent Epitopes within the First and Second Variable Domains of Human Immunodeficiency Virus Type 1 gp120" Journal of Virology 1993 67(8):4932-4944.
Pinter et al. "The C108g Epitope in the V2 Domain of gp120 Functions as a Potent Neutralization Target When Introduced into Envelope Proteins Derived from Human Immunodeficiency Virus Type 1 Primary Isolates" Journal of Virology 2005 79(11):6909-6917.
Pinter et al. "The V1/V2 Domain of gp120 Is a Global Regulator of the Sensitivity of Primary Human Immunodeficiency Virus Type 1 Isolates to Neutralization by Antibodies Commonly Induced upon Infection" Journal of Virology 2004 78(10):5205-5215.
Shotton et al. "Identification and Characterization of Monoclonal Antibodies Specific for Polymorphic Antigenic Determinants within the V2 Region of the Human Immunodeficiency Virus Type 1 Envelope Glycoprotein" Journal of Virology 1995 69(1):222-230.
Vijh-Warrier et al. "Characterization of the Variable Regions of a Chimpanzee Monoclonal Antibody with Potent Neutralizing Activity against HIV-1" Molecular Immunology 1995 32(14/15):1081-1092.
Warrier et al. "A Novel, Glycan-Dependent Epitope in the V2 Domain of Human Immunodeficiency Virus Type 1 gp120 Is Recognized by a Highly Potent, Neutralizing Chimpanzee Monoclonal Antibody" Journal of Virology 1994 68(7):4636-4642.

(Continued)

*Primary Examiner* — Jeffrey Parkin
(74) *Attorney, Agent, or Firm* — Licata & Tyrrell P.C.

(57) ABSTRACT

This invention features polypeptides, variants thereof, and fragments thereof useful in eliciting an immune response (e.g., neutralizing antibodies) against a broad spectrum of HIV-1 isolates. The polypeptides, variants, and fragments include a portion of the gp120 V2 domain of HIV-1. The polypeptides, variants, and fragments display an epitope that is recognized by at least one antibody which neutralizes at least one HIV-1 primary isolate. This invention also features nucleic acid sequences encoding those polypeptides. In addition, the invention provides methods of screening for inhibitors of HIV-1 entry into cells, as well as methods of treatment using the inhibitors.

4 Claims, 5 Drawing Sheets

(56) References Cited

OTHER PUBLICATIONS

Wu et al. "Characterization of Neutralization Epitopes in the V2 Region of Human Immunodeficiency Virus Type 1 gp120: Role of Glycosylation in the Correct Folding of the V1/V2 Domain" Journal of Virology 1995 69(4):2271-2278.
Zolla-Pazner, S. "Identifying Epitopes of HIV-1 that Induce Protective Antibodies" Nature Reviews Immunology 2004 4(3):199-210.
Zwick et al. "Broadly Neutralizing Antibodies Targeted to the Membrane-Proximal External Region of Human Immunodeficiency Virus Type 1 Glycoprotein gp41" Journal of Virology 2001 75(22):10892-10905.
Office Communication dated Dec. 11, 2013 from U.S. Appl. No. 12/309,256, filed Aug. 18, 2011.
Desrosiers, R.C. "Prospects for an AIDS Vaccine" Nature Medicine 2004 10(3):221-223.
Letvin, N. L. "Progress and Obstacles in the Development of an AIDS Vaccine" Nature 2006 6:930-939.
Gallo, R.C. "The End or the Beginning of the Drive to an HIV-Preventative Vaccine: a View from Over 20 Years" The Lancet 2005 366:1894-1898.
Walker, B.D. and Burton, D.R. "Toward an AIDS Vaccine" Science 2008 320:760-764.
International Search Report from PCT/US2007/015703, Apr. 28, 2008.
International Preliminary Report on Patentability from PCT/2007/015703, Jan. 13, 2009.

\* cited by examiner

|  | | | | 10/76b | C108g | 2909 |
| --- | --- | --- | --- | --- | --- | --- |
|  | 160 | 167 | | | | |
| SF162    | GEIKNCSFKVTTSIRNKMQKEYAFFYKLDVVPIDNDNTSYKLINCNTS | - | - | +++ |
| SF162(GKV) | -----KVT----G-V---------VV--------N------IN---- | + | - | +++ |
| SF162(NI)  | -----NIT----N-M---------VV--------N------IN---- | - | - | - |
| SF162(NI+GKV) | -----NIT----G-V---------VV--------N------IN---- | + | +++ | - |
| JR-FL    | -----NIT----DEV---------VV----NN---R-IS-D----- | - | - | - |
| JR-FL(GK) | -----NIT----GKV---------VV----NN---R-IS-D----- | + | +++ | - |
| HXB2     | -----NIS----G-V---------II-----TTS---TS------- | +++ | +++ | - |

FIG. 1

|  | 160 | 168 | 2909 |
|---|---|---|---|
| SF162 | NCSFKVTTSIRNKMQKEYAFFYK | | +++ |
| SF162(GKV) | -----------G-V--------- | | + |
| JR-FL wt | ----NIT----DEV--------- | | - |
| JR-FL(K160) | ----KIT----DEV--------- | | - |
| JR-FL(K168) | ----NIT----D-V--------- | | - |
| JR-FL(SK) | ----SIT----D-V--------- | | ++ |
| JR-FL(KK) | ----KIT----D-V--------- | | ++++ |

*FIG. 3*

SEQUENCE LISTING

```
<160> NUMBER OF SEQ ID NOS: 33

<210> SEQ ID NO 1
<211> LENGTH: 30
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa denotes Met, Ile, Val, Thr or Ala
<220> FEATURE:
<221> NAME/KEY: MISC_FEATURE
<222> LOCATION: (12)..(12)
<223> OTHER INFORMATION: Xaa denotes Ser, Glu, Gly, Asn, Arg, or Asp
<220> FEATURE:
<221> NAME/KEY: MISC_FEATURE
<222> LOCATION: (13)..(13)
<223> OTHER INFORMATION: Xaa denotes Leu, Ile or Met
<220> FEATURE:
<221> NAME/KEY: MISC_FEATURE
<222> LOCATION: (17)..(19)
<223> OTHER INFORMATION: Xaa denotes Lys, Arg, or Gln
<220> FEATURE:
<221> NAME/KEY: MISC_FEATURE
<222> LOCATION: (20)..(20)
<223> OTHER INFORMATION: Xaa denotes Glu or Val
<220> FEATURE:
<221> NAME/KEY: MISC_FEATURE
<222> LOCATION: (22)..(22)
<223> OTHER INFORMATION: Xaa denotes Ser or Ala
<220> FEATURE:
<221> NAME/KEY: MISC_FEATURE
<222> LOCATION: (26)..(26)
<223> OTHER INFORMATION: Xaa denotes Lys, Arg, Ser, Thr or Asn
<220> FEATURE:
<221> NAME/KEY: MISC_FEATURE
<222> LOCATION: (29)..(29)
<223> OTHER INFORMATION: Xaa denotes Ile, Leu or Val

<400> SEQUENCE: 1

Glu Ile Lys Asn Cys Ser Phe Asn Xaa Thr Thr Xaa Xaa Arg Asp Lys
1               5                   10                  15
```

```
Xaa Xaa Xaa Xaa Tyr Xaa Leu Phe Tyr Xaa Leu Asp Xaa Val
        20              25              30
```

<210> SEQ ID NO 2
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(6)
<223> OTHER INFORMATION: Xaa denotes Lys, Arg or Gln
<220> FEATURE:
<221> NAME/KEY: MISC_FEATURE
<222> LOCATION: (7)..(7)
<223> OTHER INFORMATION: Xaa denotes Glu or Val

<400> SEQUENCE: 2

```
Arg Asp Lys Xaa Xaa Xaa Xaa
1               5
```

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

```
Lys Gln Lys Val
1
```

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

```
Lys Gln Lys Glu
1
```

<210> SEQ ID NO 5
<211> LENGTH: 48
<212> TYPE: PRT
<213> ORGANISM: Artificial sequence
<220> FEATURE:
<223> OTHER INFORMATION: Synthetic peptide

<400> SEQUENCE: 5

```
Gly Glu Ile Lys Asn Cys Ser Phe Lys Val Thr Thr Ser Ile Arg Asn
1               5                   10                  15

Lys Met Gln Lys Glu Tyr Ala Phe Phe Tyr Lys Leu Asp Val Val Pro
            20                  25                  30

Ile Asp Asn Asp Asn Thr Ser Tyr Lys Leu Ile Asn Cys Asn Thr Ser
        35                  40                  45
```

<210> SEQ ID NO 6
<211> LENGTH: 48
<212> TYPE: PRT
<213> ORGANISM: Artificial sequence
<220> FEATURE:
<223> OTHER INFORMATION: Synthetic peptide

<400> SEQUENCE: 6

-continued

```
Gly Glu Ile Lys Asn Cys Ser Phe Lys Val Thr Thr Ser Ile Arg Gly
1               5                   10                  15

Lys Val Gln Lys Glu Tyr Ala Phe Phe Tyr Lys Leu Asp Val Val Pro
            20                  25                  30

Ile Asp Asn Asp Asn Thr Ser Tyr Lys Leu Ile Asn Cys Asn Thr Ser
        35                  40                  45
```

<210> SEQ ID NO 7
<211> LENGTH: 48
<212> TYPE: PRT
<213> ORGANISM: Artificial sequence
<220> FEATURE:
<223> OTHER INFORMATION: Synthetic peptide

<400> SEQUENCE: 7

```
Gly Glu Ile Lys Asn Cys Ser Phe Asn Ile Thr Thr Ser Ile Arg Met
1               5                   10                  15

Lys Met Gln Lys Glu Tyr Ala Phe Phe Tyr Lys Leu Asp Val Val Pro
            20                  25                  30

Ile Asp Asn Asp Asn Thr Ser Tyr Lys Leu Ile Asn Cys Asn Thr Ser
        35                  40                  45
```

<210> SEQ ID NO 8
<211> LENGTH: 48
<212> TYPE: PRT
<213> ORGANISM: Artificial sequence
<220> FEATURE:
<223> OTHER INFORMATION: Synthetic peptide

<400> SEQUENCE: 8

```
Gly Glu Ile Lys Asn Cys Ser Phe Asn Ile Thr Thr Ser Ile Arg Gly
1               5                   10                  15

Lys Val Gln Lys Glu Tyr Ala Phe Phe Tyr Lys Leu Asp Val Val Pro
            20                  25                  30

Ile Asp Asn Asp Asn Thr Ser Tyr Lys Leu Ile Asn Cys Asn Thr Ser
        35                  40                  45
```

<210> SEQ ID NO 9
<211> LENGTH: 48
<212> TYPE: PRT
<213> ORGANISM: Artificial sequence
<220> FEATURE:
<223> OTHER INFORMATION: Synthetic peptide

<400> SEQUENCE: 9

```
Gly Glu Ile Lys Asn Cys Ser Phe Asn Ile Thr Thr Ser Ile Arg Asp
1               5                   10                  15

Glu Val Gln Lys Glu Tyr Ala Phe Phe Tyr Lys Leu Asp Val Val Pro
            20                  25                  30

Ile Asp Asn Asn Asn Thr Ser Tyr Arg Leu Ile Ser Cys Asp Thr Ser
        35                  40                  45
```

<210> SEQ ID NO 10
<211> LENGTH: 48
<212> TYPE: PRT
<213> ORGANISM: Artificial sequence
<220> FEATURE:
<223> OTHER INFORMATION: Synthetic peptide

<400> SEQUENCE: 10

```
Gly Glu Ile Lys Asn Cys Ser Phe Asn Ile Thr Thr Ser Ile Arg Gly
1               5                   10                  15
```

```
Lys Val Gln Lys Glu Tyr Ala Phe Phe Tyr Lys Leu Asp Val Val Pro
            20                  25                  30

Ile Asp Asn Asn Asn Thr Ser Tyr Arg Leu Ile Ser Cys Asp Thr Ser
        35                  40                  45
```

<210> SEQ ID NO 11
<211> LENGTH: 48
<212> TYPE: PRT
<213> ORGANISM: Artificial sequence
<220> FEATURE:
<223> OTHER INFORMATION: Synthetic peptide

<400> SEQUENCE: 11

```
Gly Glu Ile Lys Asn Cys Ser Phe Asn Ile Ser Thr Ser Ile Arg Gly
1               5                   10                  15

Lys Val Gln Lys Glu Tyr Ala Phe Phe Tyr Lys Leu Asp Ile Ile Pro
            20                  25                  30

Ile Asp Asn Asp Thr Thr Ser Tyr Lys Leu Thr Ser Cys Asn Thr Ser
        35                  40                  45
```

<210> SEQ ID NO 12
<211> LENGTH: 23
<212> TYPE: PRT
<213> ORGANISM: Artificial sequence
<220> FEATURE:
<223> OTHER INFORMATION: Synthetic peptide

<400> SEQUENCE: 12

```
Asn Cys Ser Phe Lys Val Thr Thr Ser Ile Arg Asn Lys Met Gln Lys
1               5                   10                  15

Glu Tyr Ala Phe Phe Tyr Lys
            20
```

<210> SEQ ID NO 13
<211> LENGTH: 23
<212> TYPE: PRT
<213> ORGANISM: Artificial sequence
<220> FEATURE:
<223> OTHER INFORMATION: Synthetice peptide

<400> SEQUENCE: 13

```
Asn Cys Ser Phe Lys Val Thr Thr Ser Ile Arg Gly Lys Val Gln Lys
1               5                   10                  15

Glu Tyr Ala Phe Phe Tyr Lys
            20
```

<210> SEQ ID NO 14
<211> LENGTH: 23
<212> TYPE: PRT
<213> ORGANISM: Artificial sequence
<220> FEATURE:
<223> OTHER INFORMATION: Synthetic peptide

<400> SEQUENCE: 14

```
Asn Cys Ser Phe Lys Ile Thr Thr Ser Ile Arg Asp Glu Val Gln Lys
1               5                   10                  15

Glu Tyr Ala Phe Phe Tyr Lys
            20
```

<210> SEQ ID NO 15
<211> LENGTH: 23
<212> TYPE: PRT
<213> ORGANISM: Artificial sequence
<220> FEATURE:

-continued

<223> OTHER INFORMATION: Synthetic peptide

<400> SEQUENCE: 15

Asn Cys Ser Phe Asn Ile Thr Thr Ser Ile Arg Asp Lys Val Gln Lys
1               5                   10                  15
Glu Tyr Ala Phe Phe Tyr Lys
            20

<210> SEQ ID NO 16
<211> LENGTH: 23
<212> TYPE: PRT
<213> ORGANISM: Artificial sequence
<220> FEATURE:
<223> OTHER INFORMATION: Synthetic peptide

<400> SEQUENCE: 16

Asn Cys Ser Phe Ser Ile Thr Thr Ser Ile Arg Asp Lys Val Gln Lys
1               5                   10                  15
Glu Tyr Ala Phe Phe Tyr Lys
            20

<210> SEQ ID NO 17
<211> LENGTH: 23
<212> TYPE: PRT
<213> ORGANISM: Artificial sequence
<220> FEATURE:
<223> OTHER INFORMATION: Synthetic peptide

<400> SEQUENCE: 17

Asn Cys Ser Phe Lys Ile Thr Thr Ser Ile Arg Asp Lys Val Gln Lys
1               5                   10                  15
Glu Tyr Ala Phe Phe Tyr Lys
            20

<210> SEQ ID NO 18
<211> LENGTH: 35
<212> TYPE: PRT
<213> ORGANISM: Artificial sequence
<220> FEATURE:
<223> OTHER INFORMATION: Synthetic peptide

<400> SEQUENCE: 18

Cys Thr Arg Pro Asn Asn Asn Thr Arg Lys Ser Ile Thr Ile Gly Pro
1               5                   10                  15
Gly Arg Ala Phe Tyr Ala Thr Gly Asp Ile Ile Gly Asp Ile Arg Gln
            20                  25                  30
Ala His Cys
        35

<210> SEQ ID NO 19
<211> LENGTH: 35
<212> TYPE: PRT
<213> ORGANISM: Artificial sequence
<220> FEATURE:
<223> OTHER INFORMATION: Synthetice peptide

<400> SEQUENCE: 19

Cys Thr Arg Pro Asn Asn Asn Thr Arg Lys Ser Ile Arg Ile Gly Pro
1               5                   10                  15
Gly Gln Thr Phe Tyr Ala Thr Gly Asp Ile Ile Gly Asp Ile Arg Gln
            20                  25                  30
Ala His Cys
        35

<210> SEQ ID NO 20
<211> LENGTH: 35
<212> TYPE: PRT
<213> ORGANISM: Artificial sequence
<220> FEATURE:
<223> OTHER INFORMATION: Synthetic peptide

<400> SEQUENCE: 20

Cys Thr Arg Pro Asn Asn Asn Thr Arg Lys Ser Ile Arg Ile Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 21
<211> LENGTH: 35
<212> TYPE: PRT
<213> ORGANISM: Artificial sequence
<220> FEATURE:
<223> OTHER INFORMATION: Synthetic peptide

<400> SEQUENCE: 21

Cys Thr Arg Pro Asn Asn Asn Thr Arg Lys Ser Ile His Ile Gly Pro
1               5                   10                  15

Gly Gln Ala Phe Tyr Ala Thr Gly Glu Ile Ile Gly Asp Ile Arg Lys
            20                  25                  30

Ala His Cys
        35

<210> SEQ ID NO 22
<211> LENGTH: 35
<212> TYPE: PRT
<213> ORGANISM: Artificial sequence
<220> FEATURE:
<223> OTHER INFORMATION: Synthetic peptide

<400> SEQUENCE: 22

Cys Thr Arg Pro Asn Asn Asn Thr Arg Lys Ser Val Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 23
<211> LENGTH: 35
<212> TYPE: PRT
<213> ORGANISM: Artificial sequence
<220> FEATURE:
<223> OTHER INFORMATION: Synthetic peptide

<400> SEQUENCE: 23

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

<210> SEQ ID NO 24

```
<211> LENGTH: 35
<212> TYPE: PRT
<213> ORGANISM: Artificial sequence
<220> FEATURE:
<223> OTHER INFORMATION: Synthetic peptide

<400> SEQUENCE: 24

Cys Thr Arg Pro Asn Asn Asn Thr Arg Lys Ser Ile His Leu Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 25
<211> LENGTH: 35
<212> TYPE: PRT
<213> ORGANISM: Artificial sequence
<220> FEATURE:
<223> OTHER INFORMATION: Synthetic peptide

<400> SEQUENCE: 25

Cys Thr Arg Pro Ser Asn Asn Thr Arg Thr Ser Ile Thr Ile Gly Pro
1               5                   10                  15

Gly Gln Val Phe Tyr Arg Thr Gly Asp Ile Ile Gly Asp Ile Arg Lys
            20                  25                  30

Ala Tyr Cys
        35

<210> SEQ ID NO 26
<211> LENGTH: 4
<212> TYPE: PRT
<213> ORGANISM: Artificial sequence
<220> FEATURE:
<223> OTHER INFORMATION: Synthetic peptide

<400> SEQUENCE: 26

Lys Lys Lys Glu
1

<210> SEQ ID NO 27
<211> LENGTH: 4
<212> TYPE: PRT
<213> ORGANISM: Artificial sequence
<220> FEATURE:
<223> OTHER INFORMATION: Synthetic peptide

<400> SEQUENCE: 27

Lys Lys Lys Val
1

<210> SEQ ID NO 28
<211> LENGTH: 4
<212> TYPE: PRT
<213> ORGANISM: Artificial sequence
<220> FEATURE:
<223> OTHER INFORMATION: Synthetic peptide

<400> SEQUENCE: 28

Lys Arg Gln Glu
1

<210> SEQ ID NO 29
<211> LENGTH: 4
<212> TYPE: PRT
```

```
<213> ORGANISM: Artificial sequence
<220> FEATURE:
<223> OTHER INFORMATION: Synthetic peptide

<400> SEQUENCE: 29

Lys Arg Lys Val
1

<210> SEQ ID NO 30
<211> LENGTH: 4
<212> TYPE: PRT
<213> ORGANISM: Artificial sequence
<220> FEATURE:
<223> OTHER INFORMATION: Synthetic peptide

<400> SEQUENCE: 30

Lys Lys Gln Val
1

<210> SEQ ID NO 31
<211> LENGTH: 4
<212> TYPE: PRT
<213> ORGANISM: Artificial sequence
<220> FEATURE:
<223> OTHER INFORMATION: Synthetic peptide

<400> SEQUENCE: 31

Lys Lys Gln Glu
1

<210> SEQ ID NO 32
<211> LENGTH: 23
<212> TYPE: PRT
<213> ORGANISM: Artificial sequence
<220> FEATURE:
<223> OTHER INFORMATION: Synthetic peptide

<400> SEQUENCE: 32

Asn Cys Ser Phe Asn Ile Thr Thr Ser Ile Arg Asp Glu Val Gln Lys
1               5                   10                  15

Glu Tyr Ala Phe Phe Tyr Lys
            20

<210> SEQ ID NO 33
<211> LENGTH: 5
<212> TYPE: PRT
<213> ORGANISM: Artificial sequence
<220> FEATURE:
<223> OTHER INFORMATION: Synthetic peptide

<400> SEQUENCE: 33

Gly Gly Gly Gly Ser
1               5
```

NEUTRALIZING ANTIBODIES THAT BIND TO THE HIV-1 ENV V2 CRITICAL NEUTRALIZATION DOMAIN

INTRODUCTION

This application is a divisional of U.S. Ser. No. 12/309,256 filed Aug. 18, 2011, which is a 371 application of PCT/US2007/015703 filed Jul. 10, 2007, which is based on U.S. Provisional Ser. No. 60/830,044 filed Jul. 10, 2006, the teachings of which are incorporated herein by reference in their entireties.

CLAIM OF PRIORITY

This application claims benefit of U.S. Provisional Patent Application No. 60/830,044, filed Jul. 10, 2006, incorporated herein by reference.

STATEMENT AS TO FEDERALLY FUNDED RESEARCH

This invention was made with government support under grant numbers AI46283 and AI50452 awarded by U.S. Public Health Service. The government has certain rights in the invention.

TECHNICAL FIELD

This invention relates to Human Immunodeficiency virus 1 (HIV-1) polypeptides and, in particular, HIV-1 polypeptides useful in eliciting cross-neutralizing antibodies.

BACKGROUND OF THE INVENTION

Despite much progress in recent years towards the characterization of functional regions of HIV-1 Envelope protein (Env) and in defining major neutralizing epitopes, progress towards an HIV-I vaccine capable of inducing a protective Immoral response has been limited (Zolla-Pazner et al. (2004) Nat. Rev. Immunol. 4(3):199-210; Burton et al. (2004) Nat. Rev. Immunol. 5(3):233-236). There is now a realization that typical antibodies generated in response to infection or immunization with standard Env proteins do not possess appreciable neutralizing activities for common clinical or primary HIV-1 isolates, even when these antibodies are directed against neutralization epitopes present in the target viruses. One mechanism for this resistance appears to be the shielding of sensitive neutralization domains in intact virions by specific regions and structural features of HIV-1 clinical isolate SU (HIV-1 SU), located in the V1/V2 region (Pinter at al. (2004) J. Virol. 78(10):5205-5215). The highly effective masking of sensitive neutralization sites by the V1/V2 domain poses a major conundrum for HIV-1 vaccine development. The limited number of known neutralization targets that are insensitive to such masking, are poorly immunogenic. A few exceptional monoclonal antibodies (mAbs) have been identified that are not sensitive to such effects and possess broad neutralizing activities for primary isolates. These include the HIV-1 gp120-specific mABs b12 and 2G12 (Burton et al. (2004) Nat. Rev. Immunol. 5(3): 233-236), and gp41-specific mAbs 2F5 and 4E10 (Zwick et al. (2001) 75(22):10892-10905; Mined et al. (2004) AIDS Res. Hum. Retroviruses 20(7):755-762). However, these mAbs possess unusual structures, including unusually large CDR3 regions or have autoreactive properties (Haynes et al., (2005) Science 308(5730):1906-1908), and antibodies against these epitopes are rarely produced in immunized or infected individuals.

Thus, it is important to identify additional immunogenic targets that can mediate potent neutralization, while also being reasonably well conserved or present in a limited number of allelic forms that can be formulated into a multivalent vaccine.

SUMMARY OF THE INVENTION

The current invention describes a region in the V2 domain that is semi-conserved, and has been shown in several cases to contain target epitopes for mAbs that possess very potent neutralizing activities. The epitopes in this region that determine this activity are referred to as the V2-Critical Neutralization Domain (V2-CND). The invention describes variant V2 sequences that express more representative versions of the V2-CND that can induce antibodies that possess potent neutralizing activities for multiple HIV-1 isolates. This contrasts the general consensus in the field that any neutralizing targets in V1 or V2 are highly type-specific, and limited to a single or at most a very limited number of viral sequences, and thus not of any importance in an HIV vaccine {Burton, 2004 #2237; Burton, 2005 #2675; Pantophlet, 2006 #2709; Zolla-Pazner, 2004 #2271}.

Many proteins which include a GP120 V1/V2 of an HIV-1 strain are known, i.e., those disclosed in U.S. Pat. No. 6,815,201, which display an epitope which is recognized by an antibody which neutralizes at least one HIV-1 primary isolate.

This invention relates to a certain sub-set of such proteins in V2 that display epitopes that are sensitive neutralization targets. The semi-conserved nature of this region suggests that some of these targets may be recognized by antibodies that react with multiple viral sequences. Accordingly these targets are of increased importance in an HIV vaccine.

The invention is based in part on the identification of overlapping specificity determinants of HIV-1 recognized by two highly potent neutralizing antibodies (2909 and C1806g), both of which are present in the V2 region of HIV-1 Env protein. Analysis of substitution mutations in the V2 region, using two different HIV-1 isolates, revealed that the minimal epitopes for 2909 and C108g varied from the Glade B consensus sequence only at single positions (position 8 in SEQ ID NO:1 for 2909 and position 15 in SEQ ID NO:1 for C108g). Introducing key substitutions in V2 into both JR-FL and YU2 HIV-1 isolate Env proteins, normally insensitive to neutralization by 2909 or C108g, resulted in extremely sensitive neutralization by both antibodies. This showed that the region determining the specificity of 2909 and C108g is very sensitive to neutralization, and that the type-specificity of these antibodies is due to the presence of rare substitutions at the key positions. Thus the polypeptide of the invention comprises a sequence that contains a consensus residue at at least one, and preferably, both of these positions.

In addition, it has been found that the neighboring sequences at positions 9,12,13, and 17-20 of the consensus-containing polypeptide of the invention is polymorphic, suggesting the presence of multiple allelic versions of neutralization epitopes in this region.

Accordingly, the epitope-containing polypeptide, (the V2 Critical Neutralizing Domain, or V2-CND), depicted in SEQ ID NO:1, is believed to describe multiple variants in this region that are both immunogenic and capable of mediating the production of antibodies with potent and cross-neutralizing activities against HIV-1.

In one embodiment, the invention relates to an isolated polypeptide, consisting of an amino acid sequence, 30 amino acids in length, and of sequence EIKNC SFNXT TXXRD KXXXX YXLFY XLDXV (SEQ ID NO:1). The X at position 9 of SEQ ID NO:1 can be M or I; the X at position 12 of SEQ ID NO:1 can be S, E, G, or N; the X at position 13 can be L, I, or M; the X at position 17 of SEQ ID NO:1 can be K, R or Q; the X at position 18 of SEQ ID NO:1 can be K, R, or Q; the X at position 19 of SEQ ID NO:1 can be K, R or Q; the X at position 20 of SEQ ID NO:1 can be E or V; the X at position 22 of SEQ ID NO:1 can be S or A; the X at position 26 of SEQ ID NO:1 can be K or R; and the X at position 29 of SEQ ID NO:1 can be I or V.

In another embodiment the invention relates to a fragment of the V2-CND sequence of SEQ ID NO:1. The fragment can contain (a) amino acids 14-20 of SEQ ID NO:1 (RD-KXXXX), or (b) at least six consecutive amino acids of SEQ ID NO:1, including at least two of the three residues at positions 14-16 and at least two of the X residues at positions 17-20 as defined above. The V2-CND polypeptide or a fragment thereof can include R, D, and K residues of positions 14-16, and the residues at positions 17-20 as depicted by SEQ ID NO:1.

More particularly the V2-CND polypeptide as depicted by SEQ ID NO:1 also includes amino acid sequences where (i) the X at position 17 can be K, the X at position 18 can be Q, the X at position 19 can be K, and the X at position 20 can be V (KQKV); (ii) the X at position 17 can be K, the X at position 18 can be Q, the X at position 19 can be K, and the X at position 20 can be E (KQKE); (iii) the X at position 17 can be K, the X at position 18 can be K, and the X at position 19 can be K (KKK); (iv) the X at position 17 can be K, the X at position 18 can be R, and the X at position 19 can be Q (KRQ); (v) the X at position 17 can be K, the X at position 18 can be K, and the X at position 19 can be Q (KKQ); or (vi) the X at position 17 can be K, the X at position 18 can be Q, and the X at position 19 can be Q (KQQ). The X at position 20 as depicted in SEQ ID NO:1 can be V or E.

The V2-CND polypeptide or a fragment thereof can be a synthetic, or recombinant molecule, or can be a hybrid polypeptide flanked at one or both ends of the molecule with either additional sequences that normally flank this region in gp120, or with heterologous sequences (e.g., one portion of a polypeptide consisting of the V2-CND polypeptide or a fragment of the V2-CND polypeptide and, covalently-linked to it, a second portion of the polypeptide that is heterologous sequence). As used herein, "heterologous sequence" refers to any amino acid sequence outside of the natural context in which this polypeptide could occur (e.g., HIV-1 gp120 or gp160 polypeptide). This sequence could be, for example, an antigenic tag (e.g., FLAG, polyhistidine, hemagluttanin (HA), glutathione-S-transferase (GST), or maltose-binding protein (MBP)). Heterologous sequence could also include polypeptides or portions of polypeptides useful in generating or enhancing immune responses (e.g., interleukin-2, interleukin-4, interferon gamma, or T-helper sequences), or in the targeting of the polypeptide to specific locations (e.g., immunoglobulins).

The V2-CND polypeptide or a fragment thereof can also be glycosylated. The glycosylated polypeptide or fragment thereof can be N-glycosylated at one or both of the N (asparagine) amino acids at positions 4 and 8 of SEQ ID NO:1. In some embodiments of the V2-CND polypeptide or fragment thereof, the C residue at position 6 of SEQ ID NO:1 can serve as the first member of a disulfide linkage to another macromolecule. The macromolecule can be another V2-CND polypeptide (e.g., thus resulting in a homodimer) or fragment thereof, or it can be a non-V2-CND polypeptide. This C residue can also be substituted by another residue, such as serine, so that a disulfide bond in not formed at this position.

Yet other embodiments are pharmaceutical compositions containing the V2-CND polypeptide, or a fragment thereof, and a pharmaceutically acceptable carrier.

Also provided by the invention is an isolated antibody, or antigen-binding-fragment thereof, that specifically binds to HIV-1 gp120 at a sequence that includes SEQ ID NO: 2, and whose binding is dependent on one or more (e.g., 2, 3, 4, 5 or 6) of the amino acid residues at positions 14-19 of SEQ ID NO:1. The amino acids at positions 17-19 of SEQ ID NO:1 recognized by the antibody or antigen-binding fragment thereof can be also be KQKE, KQKV, KKKE, KKKV, KRQE, KRKV, KKQV, or KKQE. Antibody binding can be dependent on the presence of at least two of the R, D, and K amino acid residues at positions 14-16 of SEQ ID NO:1, and at least two of the amino acid residues at positions 17-19 of SEQ ID NO:1. Also provided is an isolated antibody or an antigen-binding-fragment thereof that crossblocks the binding of the aforementioned V2-CND-specific antibody or an antigen-binding-fragment thereof.

The invention also relates to a nucleic acid that encodes the V2-CND polypeptides or fragment thereof. Also provided is a vector containing a nucleic acid encoding the V2-CND polypeptides or fragments thereof. The vector can also contain an expression control sequence that is operably-linked to the nucleic acid. The vector can, optionally, include more than one V2-CND polypeptide or fragment thereof.

In another embodiment, the invention features a cell containing any of the aforementioned nucleic acids or nucleic acid vectors. The cell can be a prokaryotic cell (e.g., a bacterial cell) or a eukaryotic cell (e.g., a yeast, insect, or mammalian cell). The cell can also be a human cell.

Also embodied herein are methods of producing a V2-CND polypeptide or fragment thereof. The method involves culturing a cell containing a vector, which contains a nucleic acid encoding any of the V2-CND polypeptides or fragments thereof described herein, operably-linked to an expression control sequence, under conditions that allow for expression of the polypeptides or fragments. The method can also include the step of recovering the polypeptides or fragments from the cell culture. Such recovering from the culture can include recovery from the cells (e.g., from purified cells or cell extracts) or, where a peptide is secreted or otherwise released from a cell, the V2-CND polypeptide or fragments can be recovered from the cell culture media.

Also embodied herein is a method of stimulating the production in a mammalian subject of an antibody whose binding in dependent on sequences contained in the V2-CND and that neutralizes more than one HIV-1 strain. The method includes the step of delivering to a mammalian subject a composition containing, or consisting of, any of the V2-CND polypeptides or fragments thereof described herein. The term "delivering" refers to any method (e.g., self-delivery, inhalation, skin contact, or direct administration) by which a subject would come in contact with a composition described herein. Delivery of the V2-CND-containing polypeptide or fragment thereof to the mammalian subject can involve the administration of the composition to the mammalian subject. The method can also involve further administering a composition containing one or more additional V2-CND polypeptides or fragments thereof described herein to the mammalian subject. As mentioned above, the V2-CND polypeptides or their fragments can also contain heterologous sequence(s) at one or both ends. In some aspects, the heterologous sequence can be a single-chain epitope fused to a T-helper sequence useful in stimulating an immune response in an individual. T-helper sequences are well known to those of skill in the art and are described, for example, in Zhang et al., (2006) Expert Rev Vaccines 5(2):223-231. The T-helper sequence can be either of the sequences depicted in SEQ ID NO: 3 or SEQ ID NO: 4.

Furthermore, "delivering" can include administering to the subject one or more vectors, each of which contains a nucleic acid sequence encoding any V2-CND-containing polypeptide or fragment thereof described herein, operably-linked to an expression control sequence. The vector can be administered as an isolated vector, or a composition containing the vector and a pharmaceutically acceptable carrier. The mammalian subject can be a mouse, rat, dog, cat, cow, horse, monkey, or human subject (e.g., a human patient). The compositions for use in the method can be further delivered to a subject with an immunological adjuvant. Such adjuvants are well known to those of skill in the art and include, for example, an aluminum salt or oil in water and an emulsifying agent, any one of a combination of immunostimulating agents or combinations thereof. The V2-CND-containing polypeptides, their fragments, nucleic acids encoding the V2-CND polypeptides or their fragments described herein, and compositions thereof can be administered as compositions of polypeptides and/or nucleic acids having one component that elicits an immune response primarily against macrophage-tropic HIV-1 strains and a second component that elicits an immune response primarily against T cell tropic HIV-1 strains. It may also be desirable for either or both components to be composed of a mixture of antigens, e.g., a mixture of antigens each of which elicits an immune response to a particular HIV-1 strain or group of HIV-1 strains.

Also provided is a method of generating a compound that binds to the V2-CND region of HIV-1 gp120. The method includes the steps of: (i) designing, based on the 3-dimensional structure of the V2-CND polypeptide, a compound containing a region that has the potential to bind to the V2-CND region of HIV-1 gp120; and (ii) synthesizing the compound. The method can include the additional step of determining whether the compound inhibits infection of a cell by at least one HIV-1 isolate. Furthermore, featured herein is a method or process of manufacturing a compound. The method includes after determining that the generated compound that binds to the V2-CND region of HIV-1 gp120 inhibits infection of a cell by at least one HIV-1 isolate, manufacturing the compound. This invention also embraces a compound generated and/or manufactured by the above methods.

Also embodied in the invention is a method of inhibiting infection of a cell by HIV-1 by contacting a cell and/or an HIV-1 virus with any of the V2-CND polypeptides, fragments or compositions thereof described herein. The method can be an in vitro or an in vivo method. The cell can be a mammalian cell (e.g., a mouse, rat, guinea pig, rabbit, dog, cat, horse, goat, cow, monkey, or human cell). The HIV-1 virus can be of any clade, and can be a complete virion, an incomplete virion (e.g., a pseudovirus or empty viral particle).

Another aspect of the invention is a method of treating a subject that is infected, is suspected of being infected, or is likely to become infected with HIV-1. The method includes delivering to a subject a pharmaceutical composition containing any of the V2-CND polypeptides or fragments thereof described herein and a pharmaceutically acceptable carrier. The subject can be a mammal (e.g., a mouse, rat, cat, dog, cow, horse, or monkey). The subject can be a human (e.g., a human patient).

Also provided herein is a method of identifying a compound that binds to the V2-CND region of HIV-1 gp120 and neutralizes more than one strain of HIV-1. The method includes the steps of (i) contacting any of the V2-CND polypeptides or fragments thereof described herein with a candidate compound; and (ii) detecting whether binding of the candidate compound and the V2-CND polypeptide has occurred. The detecting step can also include measuring the binding of the candidate compound and the V2-CND polypeptide. Candidate compounds that can bind to a V2-CND polypeptide can include, for example, small molecules, antibodies or antigen-binding fragments thereof, peptides, peptidomimetics, or aptamers. This invention also encompasses a compound identified by the above method to be one that binds to the V2-CND region of HIV-1 gp120.

Another aspect of the invention is a method of inhibiting infection of a cell by HIV-1. The method includes contacting in vitro a cell and/or an HIV-1 virus with any compound described herein (e.g., a compound that binds to the V2-CND region of HIV-1 gp120, or a compound found to inhibit infection of a cell by an HIV-1 virus). The cell can be a mammalian cell (e.g., a mouse, rat, cat, dog, cow, horse, monkey, or a human cell). The HIV-1 virus can be of any Glade, and can be a complete virion or an incomplete virion (e.g., a pseudovirus or an empty viral particle).

Herein is also provided a method of treating a subject having been, or likely to have been, infected with an HIV-1 virus. The method includes delivering to a subject a composition containing a compound that was determined through any of the above described methods to (a) bind to the V2-CND region of HIV-1 gp120 and to (b) inhibit the infection of a cell by HIV-1. The composition of the method can also be delivered with a pharmaceutically acceptable carrier. The pharmaceutically acceptable carrier can be a part of the composition or delivered to the subject as a separate composition. The subject can be a mammalian subject, preferably the subject is a human subject (e.g., a human patient).

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes.

In case of conflict, the present specification, including definitions, will control. In addition, the materials, methods, and examples are illustrative only and not intended to be limiting.

BRIEF DESCRIPTION OF THE DRAWINGS

FIG. 1 is an alignment of amino acid sequences of the V2 regions of SF162 and JR-FL HIV-1 viral isolate parental and mutant Envelope (Envs) proteins used to analyze expression of the C108g, 10/76b and 2909 epitopes. The HXB2 sequence in included for comparison, and the core peptide sequence for the C108g and 10/76b epitopes is boxed in. The polymorphic residues in this region of the SF162 and JR-FL sequences are highlighted in bold, and the mutations at these positions required for expression of these epitopes are indicated. N-linked glycosylation sites (NXT/S) are underlined. SF162 amino acid sequence is SEQ ID NO: 5; SF162(GKV) amino acid sequence is SEQ ID NO: 6; SF162(NI) amino acid sequence is SEQ ID NO: 7; SF162 (NI+GKV) amino acid sequence is SEQ ID NO: 8; JR-FL amino acid sequence is SEQ ID NO: 9; JR-FL(GK) amino acid sequence is SEQ ID NO: 10; and HXB2 amino acid sequence is SEQ ID NO: 11.

FIGS. 2A, 28, and 2C are a series of line graphs depicting representative neutralization curves of wild type and chimeric and variant forms of HIV-1 SF162 and JR-FL viral clinical isolate Envelope proteins (Envs) with three mAbs that are dependent for binding on sequences in the V2 domain: FIG. 2A: 2909 mAb; Wild-type SF162 gp120 (closed squares), JR-FL gp120 with SF162 V1/V2 (open circles), SF162 with GKV at positions 167-169 (closed triangles), SF162 with said GKV and NI at positions 161 and 162 (open diamonds), and SF162 with JR-FL V3 (open squares).

FIG. 3 is an alignment of the amino acid sequences of JR-FL V2 mutant Env proteins that express the 2909 epitope. Parental HIV-1 virus clinical isolate JR-FL wt is completely resistant to the 2909 antibody. Substitution of the asparagine at 160 with the corresponding lysine present in the SF162 sequence did not, alone, confer sensitivity to 2909 antibody. However, a double mutant of N160K and K168 resulted in a JR-FL Env that was more sensitive to 2909 Ab than was SF162 Env. SF162 amino acid sequence is SEQ ID NO: 12; SF162(GKV) amino acid sequence is SEQ ID NO: 13; JR-FL(K160) amino acid sequence is SEQ ID NO: 14; JR-FL(K168) amino acid sequence is SEQ ID NO: 15; JR-FL(SK) amino acid sequence is SEQ ID NO: 16; JR-FL (KK) amino acid sequence is SEQ ID NO: 17.

DETAILED DESCRIPTION OF THE INVENTION

V2-CND Polypeptide

Figure 2A:
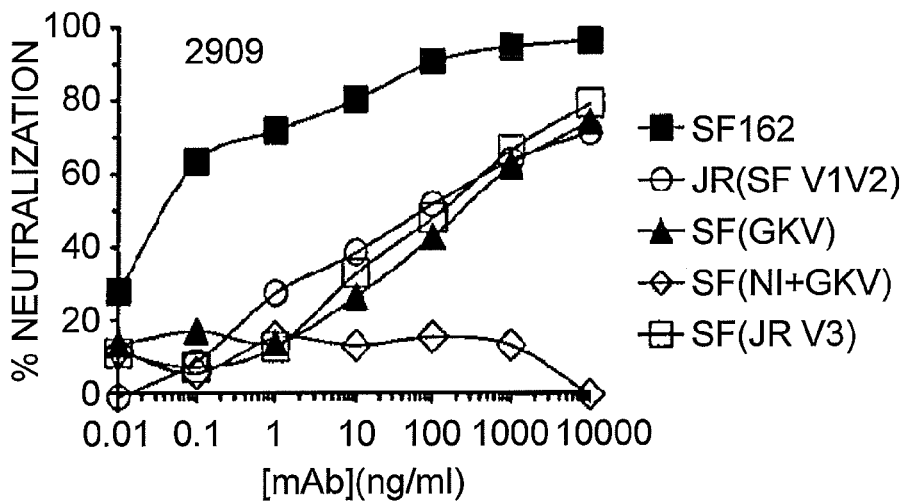

This invention relates to an isolated polypeptide (i.e., the V2-CND polypeptide), containing an amino acid sequence, 30 amino acids in length, and of sequence EIKNC SFNXT TXXRD KXXXX YXLFY XLDXV (SEQ ID NO:1), wherein the X at position 9 of SEQ ID NO:1 is M or I; the X at position 12 of SEQ ID NO:1 is S, E, G, or N; the X at position 13 of SEQ ID NO:1 is L, I, or M; the X at positions 17-19 of SEQ ID NO:1 is K, R or Q; the X at position 20 of SEQ ID NO:1 is E or V; the X at position 22 of SEQ ID NO:1 is S or A; the X at position 26 of SEQ ID NO:1 is K or R; and the X at position 29 of SEQ ID NO:1 is I or V. Moreover, the V2-CND polypeptide (SEQ ID NO:1) can also include a polypeptide where the X at position 9 of SEQ ED NO:1 is a V, T, or A; the X at position 12 of SEQ ID NO:1 is R, D, or E; the X at position 26 of SEQ ID NO:1 is S, T, or N; and the X at position 29 of SEQ ID NO:1 is an L.

The invention also relates to a fragment of the V2-CND polypeptide (SEQ ID NO:1), wherein the fragment includes amino acids 14-20 of SEQ ID NO:1. Also provided by the invention is a fragment of the V2-CND polypeptide that contains at least six consecutive amino acids of SEQ ID NO:1 and includes at least two of the residues at positions 14-16 and at least two of the X residues at positions 17-20 as defined above. The fragments can be of any length, shorter than full length V2-CND provided it is at least 6 amino acids in length. In related aspects of the invention, fragments of the V2-CND polypeptide can include amino acid sequences in which one or more amino acids are deleted and/or added to the polypeptide Fragments of the V2-CND polypeptide also include degradation products of the polypeptide which may be produced by or in a host cell.

The V2-CND polypeptide, or fragments thereof, of the invention preferably has It, D, and K residues of positions 14-16 respectively, and any of the possible residues indicated above for positions 17-20 of SEQ ID NO:1. In some of these embodiments, the amino acid sequence at positions 17-19 of SEQ ID NO:1 is KQK, KKK, KRQ, KKQ, or KKQ. In related embodiments of the V2-CND polypeptide or fragments thereof, the amino acid at position 20 of SEQ ID NO:1 is V or E.

The V2-CND polypeptide or a fragment thereof can be synthetic (e.g., synthesized using a chemical synthesizer, see for example, Miranda et al. (1999) Proc. Natl. Acad. Sci. USA 96:1181-1186). The synthesis of short amino acid sequences is well established in the peptide art. See, e.g., Stewart, et al., Solid Phase Peptide Synthesis (2d ed., 1984).

The V2-CND polypeptide or a fragment thereof can also be a recombinant molecule (e.g., cloned and expressed in bacteria, yeast, or other suitable host (see below)), and can be hybrid molecules flanked at one or both ends of the molecule with either additional natural gp120-derived sequences, or with heterologous sequences (e.g., with one portion, for example, consisting of the V2-CND polypeptide or a portion of the V2-CND polypeptide, and a second portion encoded by heterologous sequence). Heterologous sequence refers to any amino acid sequence outside of the natural context in which this polypeptide could occur (e.g., HIV-1 gp120 or gp160 polypeptide). This sequence could be, for example, an antigenic tag (e.g., FLAG, polyhistidine, hemagluttanin (HA), glutathione-S-transferase (GST), or maltose-binding protein (MBP)). Heterologous sequence can be of varying length and in some cases could be a larger sequences than the V2-CND polypeptide. Heterologous sequence could also include polypeptides or portions of polypeptides useful in generating or enhancing immune responses (e.g., interleukin-2, interleukin-4, interferon gamma, B-cell helper sequences or T-helper sequences), or in the targeting of the polypeptide to specific locations (e.g., immunoglobulins or Fc portions of immunoglobulins). In other aspects of the invention, the V2-CND polypeptides or fragments thereof can be linked to secretory, leader sequences, pro- or pre-pro sequences. In addition, heterologous sequences can include a sequence that enhances the solubility of the polypeptide, such sequences including, for example, all or part of an immunoglobulin (IgG) molecule (e.g., the constant region of an immunoglobulin heavy chain).

The V2-CND polypeptide can be modified by conjugation of additional functional moieties. Examples of such moieties include: biotin, streptavidin, fluorescein, antibodies, fragments, or antigen-binding fragments thereof. Other moieties embraced by the invention are radiolabels (e.g., $^{32}P$, $^{3}H$, $^{35}S$, $^{125}I$), chemical toxins, or chemotherapeutics (e.g., compounds useful in treatment of an HIV-1 infection).

In other embodiments, the polypeptides or fragments thereof of the invention can be also be modified by glycosylation. In particular embodiments of the invention, the glycosylated polypeptides or fragments thereof can be N-glycosylated at one or both of the at N amino acids at positions 4 and 8. Any serine (S), threonine ('F), or tyrosine (Y) residues of the polypeptides can also be O-glycosylated. The C residue at position 6 of SEQ ID NO:1 can also serve as one member of a disulfide linkage to another macromolecule. This additional macromolecule can be another V2-CND polypeptide or it can be a polypeptide containing a V2-CND polypeptide (e.g., a larger V1/V2 region or the entire gp120 protein).

In additional embodiments, the V2-CND polypeptide or its variants or fragments can be modified with moieties that prevent or substantially inhibit in vivo degradation (i.e., increase in vivo stability) of the polypeptides. Examples of such modifications include, without limitation, C-terminal amidation and/or N-terminal acetylation (peptide capping), or by polyethylene-glycol modification (PEGylation) of the C-terminus (see, for example, Brinckerhoff et al. (1999) Int. J Cancer 83(3):326-334). Additional modifications useful in increasing the stability of the V2-CND polypeptide, its variants or fragments thereof, include substituting D-amino acids in place of the natural L-amino acids at one or more of any residue in the polypeptide. Such methods are described in Tugyi et al. (2005) Proc. Natl. Acad. Sci. USA 102(2): 413-418 and Hong et al. (1999) Biochem. Pharmacol. 58(11):1775-1780.

The V2-CND polypeptide, its fragments, or modified forms thereof, have the ability of eliciting an immune response in an individual when delivered or administered (e.g., in eliciting an immune response such as, a Th1-cell-mediated immunity, or cross-neutralizing antibodies specific to (bind to) at least one HIV-1 isolate).

For clarity and understanding regarding the present invention, certain terms are defined below. Additional definitions are set forth throughout the detailed description.

A "fragment of the V2-CND polypeptide" as used herein refers to a contiguous portion of the V2-CND polypeptide that is shorter in length than the full length V2-CND polypeptide of SEQ ID NO:1 that includes at least two of the three amino acid residues at residues 14-16 (e.g., R, 0, and K at positions 14-16 respectively), and at least two of the residues at positions 17-20, and is capable of inducing an immune response in a subject. The immune response can be a cell-mediated immune response (e.g., T-cell and mononuclear cell mediated, or $T_H1$ response) or a humoral immune response (e.g., a B-cell or antibody-mediated response).

An HIV-1 or human immunodeficiency virus-1, herein refers to an HIV-1 virus of any Glade (e.g., Glade A, AG, B, C, D, E, F, G, H, I, J, K, or L) or from any isolate. Clinical isolates of HIV-I featured in this invention include, for example, HIV-1 JR-FL, HIV-1 YU2, and HIV-1 SF162.

As used herein, the term "treat" or "treatment" is defined as the application, delivery, or administration of an agent (e.g., a V2-CND polypeptide or a nucleic acid encoding a V2-CND polypeptide or fragment thereof, or anti-V2-CND antibodies) to a subject (e.g., a human patient), or application, delivery, or administration to an isolated tissue or cell from a subject, e.g., a patient, which is returned to the patient (see, for example, ex vivo methods below). As used herein, "treatment" can cure, heal, alleviate, relieve, alter, remedy, ameliorate, palliate, improve, or affect the infection or symptoms of HIV-1 infection in a subject (e.g., a mammal, a human, a human subject). As used herein, a compound or agent that is "therapeutic" is a compound or agent that causes a complete abolishment of the symptoms of a disease or a decrease in the severity of the symptoms of the disease. "Prevention" means that symptoms of the disease (e.g., an HIV-1 infection) are essentially absent. As used herein, "prophylaxis" means complete prevention of the symptoms of a disease, a delay in onset of the symptoms of a disease, or a lessening in the severity of subsequently developed disease symptoms.

As used herein, "vaccine" refers to an agent that induces the immune system of the host to respond to the composition or vaccine by producing large amounts of CTLs, and/or antibodies specific for the desired antigen. Consequently, the host typically becomes at least partially immune to later infection, or at least partially resistant to developing an ongoing chronic infection, or derives at least some therapeutic benefit. In some cases, a vaccine offers complete protective immunity, where protective immunity is the resistance to specific second infection with a pathogen that follows a first infection with the pathogen, or prior treatment with a vaccine against the pathogen. A protective immunity, ideally, is complete (100%) prophylaxis (e.g., 100% prevention of a subsequent infection by a pathogen (e.g., HIV-1)), but can also be nearly complete (e.g., 70%, 75%, 80%, 85%, 90%, 95%, up to 99%).

As used herein, an amount of a polypeptide, nucleic acid, or an anti-HIV-1 antibody effective to treat a disorder, or a "therapeutically effective amount," refers to an amount that is effective, upon single or multiple dose delivery or administration to a subject, in treating a subject with HIV-I. As used herein, an amount of an agent (e.g., a V2-CND polypeptide, a nucleic acid encoding the V2-CND polypeptide, or an anti-V2-CND antibody) effective to prevent or inhibit infection with, and/or disease caused by HIV-1, or a "a prophylactically effective amount," of the antibody refers to an amount which is effective, upon single- or multiple dose administration to the subject, in inhibiting or delaying an infection of a subject by, the occurrence of the onset of, or the recurrence of, HIV-1, or reducing a symptom (e.g., reducing the severity of a symptom) thereof. "Prophylactic" can also include 100% inhibition of the aforementioned aspects of HIV-1 infection.

In the case of polypeptide sequences that are less than 100% identical to a reference sequence, the non-identical positions are preferably, but not necessarily conservative substitutions for the reference sequence. Conservative substitutions typically include substitutions within the following groups: glycine and alanine; valine, isoleucine and leucine; aspartic acid and glutamic acid; asparagines and glutamine; serine and threonine; lysine and arginine; and phenylalanine and tyrosine.

The polypeptide of the invention may also be modified (e.g., phosphorylation, glycosylation, or disulfide linkage).

The nucleic acid molecules encoding the V2-CND polypeptide of the invention, herein include cDNA, genomic DNA, synthetic DNA, or RNA, and can be double-stranded or single-stranded (i.e., either a sense or an antisense strand).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety.

Nucleic Acids Encoding the V2-CND Polypeptide, Polypeptide Expression and Purification Isolated nucleic acids, vectors, and host cell compositions that can be used, e.g., for recombinant expression of the V2-CND polypeptides, variants, and fragments thereof, and for vaccines are provided herein.

Eukaryotic host cells as are known in the art are preferably used for expression of the V2-CND polypeptides, Because certain modifications may occur in succeeding generations due to either mutation or environmental influences, such progeny may not, in fact, be identical to the parent cell, but are still included within the scope of the term as used herein. Host cells can be any eukaryotic cells (e.g., insect cells, yeast, avian cells (e.g., chicken cells, duck cells), or mammalian cells). Mammalian cells can include cultured cells or a cell line, or a primate cell such as a Vero cell. Mammalian cells can also include a human cell. Other suitable host cells such as plant cells or insect cells are known to those skilled in the art. Alternatively, the recombinant expression vector can be transcribed and translated in vitro, for example using T7 promoter regulatory sequences and T7 polymerase.

Once the vector or nucleic acid molecule containing the DNA construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of V2-CND polypeptides. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

Purification of V2-CND Polypeptides. A variety of methodologies known in the art can be utilized to obtain the polypeptides of the present invention. The polypeptides may be purified from tissues or cells which naturally produce the peptide. Alternatively, the above-described isolated nucleic acid fragments could be used to express the V2-CND polypeptide in any organism. The V2-CND polypeptides can be purified from protein extracts or membrane extracts of cells, or preferably from supernatant media of cells that express the V2-CND polypeptides in secreted forms.

One skilled in the art can readily follow known methods for isolating proteins in order to obtain the V2-CND polypeptide free of natural contaminants. These include, but are not limited to: size-exclusion chromatography, HPLC, ion-exchange chromatography, and affinity chromatography (for example, using antibodies specific for sites within the polypeptide (i.e., immuno-affinity chromatography), or a ligand that binds to an attached tag (e.g., glutathione ligand binding to a glutathione-S-transferase protein tag, or protein A binding to an immunoglobulin Fc domain tag).

Methods of Use of the V2-CND Polypeptide
Production of Antibodies

The present invention provides a HIV-1 polypeptide (V2-CND polypeptide), or fragment thereof, for use in the production of antibodies and antigen-binding fragments thereof that bind to the V2-CND polypeptide or fragments thereof. The antibodies can possess HIV-neutralizing activity, and thus be useful both for immunotherapeutic applications or as a vaccine.

Antibody Generation

Antibodies or antibody fragments that bind to a V2-CND polypeptide or fragment thereof can be generated by immunization, e.g., using an animal, or by in vitro methods such as phage display. A polypeptide that includes all or part of the V2-CND polypeptide can be used to generate an antibody or antibody fragment. For example, a full length V2-CND polypeptide with the following amino acid sequence: EIKNC SFNXT TXXRD KXXXX YXLFY XLDXV (SEQ ID NO:1), wherein the X at position 9 of SEQ ID NO:1 is M or I; the X at position 12 of SEQ ID NO:1 is S, E, G, or N; the X at position 13 of SEQ ID NO:1 is L, I, or M; the X at position 17 of SEQ ID NO:1 is K, R or Q; the X at position 18 of SEQ ID NO:1 is K, R, or Q; the X at position 19 of SEQ ID NO:1 is K, R or Q; the X at position 20 of SEQ ID NO:1 is E or V; the X at position 22 of SEQ ID NO:1 is S or A; the X at position 26 of SEQ ID NO:1 is K or R; and the X at position 29 of SEQ ID NO:1 is I or V. In addition, the V2-CND polypeptide (SEQ ID NO:1) can also include a polypeptide where the X at position 9 of SEQ ID NO:1 is a V, T, or A; the X at position 12 of SEQ ID NO:1 is R, D, or E; the X at position 26 of SEQ ID NO:1 is S, T, or N; and the X at position 29 of SEQ ID NO:1 is an L.

In some embodiments, fragments of the V2-CND polypeptide (e.g., carboxy- or amino-terminal truncations, V2-CND polypeptide length of 29-6 amino acids) can be used as an immunogen to generate antibodies that can be screened for reactivity to a V2-CND polypeptide. In some embodiments, a cell expressing all or part of a V2-CND polypeptide can be used as an immunogen to generate antibodies.

In some embodiments, an immunized animal contains immunoglobulin producing cells with natural, human, or partially human immunoglobulin loci. In some embodiments, the non-human animal includes at least a part of a human immunoglobulin gene. For example, it is possible to engineer mouse strains that are deficient in mouse antibody production and contain large fragments of the human Ig loci. Using hybridoma technology, antigen-specific monoclonal antibodies derived from the genes with the desired specificity can be produced and selected. See, e.g., XenoMouse™, Green et al. Nature Genetics 7:13-21 (1994), US 2003-0070185, U.S. Pat. No. 5,789,650, and WO 96/34096.

Non-human antibodies to a V2-CND polypeptide can also be produced, e.g., in a rodent. The non-human antibody can be humanized, e.g., as described in U.S. Pat. No. 6,602,503, EP 239 400, U.S. Pat. Nos. 5,693,761, and 6,407,213.

Fully human monoclonal antibodies that bind to a V2-CND polypeptide can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798,230. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333). They can also be isolated by cloning of EBV-immortalized B cells from infected patients, using standard techniques (Gamy et al., 1989, Proc. Natl. Acad. Sci. USA, 86:1624-1628), or recently modified versions of these methods, as described in Traggiai et al., (2004), Nature Med. 10(8):871-875.

In Vivo Methods

Uses of V2-CND-Containing Polypeptides to Induce Protective Immunity Administration V2-CND Polypeptides: The V2-CND polypeptide, fragments thereof, nucleic acids encoding the V2-CND polypeptide and/or fragments of V2-CND polypeptides, and compositions comprising the V2-CND polypeptide or encoding nucleic acids (herein referred to as V2-CND agent or agents) of the invention are useful in eliciting the production of antibodies when administered to a subject (e.g., useful as vaccines or therapeutics).

The V2-CND agents can be administered by a variety of methods known in the art. For many therapeutic or prophylactic applications, it will be appreciated by the skilled artisan, that the route and/or mode of administration will vary depending upon the desired results.

The V2-CND agents may be administered by any conventional methods including aerosol, oral, transdermal, transmucosal, intrapleural, intrathecal, or other suitable routes. Another useful mode of administration is parenteral (e.g., intravenous, subcutaneous, intraperitoneal, intramuscular). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion. For example, the V2-CND agents can be administered by intravenous infusion or injection. In another embodiment, the V2-CND agents are administered by intramuscular or subcutaneous injection.

The application of V2-CND agents can also be done by way of mucosal administration (including nasal). Various ways of such administration are known in the art. The pharmaceutical formulation for mucosal administration may be prepared as solutions in saline, employing benzyl alcohol or other suitable preservatives, absorption promoters to enhance bioavailability, fluorocarbons, and/or other solubilizing or dispersing agents known in the art.

Alternatively, other modes of administration including suppositories may be desirable.

Dosage regimens are adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Ideally, the therapeutic or prophylactic regimen can of a single dose of an appropriate V2-CND agent. However, the therapeutic or prophylactic regimen can include a plurality of doses over a period of time. The V2-CND agents of the invention can also be combined with additional appropriate doses of compounds including other epitopes of HIV-1.

Achieving one-dose efficacy can be approached through entrapment of immunogen in microparticles. For example, the absorbable suture material poly(lactide-co-glycolide) co-polymer can be fashioned into microparticles containing immunogen (see, e.g., Eldridge et al. (1991) Molec. Immunol., 28:287-294; Moore et al. (1995) Vaccine 13:1741-1749; and Men et al. (1995) Vaccine, 13:683-689). Following oral or parenteral administration, microparticle hydrolysis in vivo produces the non-toxic byproducts, lactic and glycolic acids, and releases immunogen largely unaltered by the entrapment process. Microparticle formulations can also provide primary and subsequent booster immunizations in a single administration by mixing immunogen entrapped microparticles with different release rates. Single dose formulations capable of releasing antigen ranging from less than one week to greater than six months can be readily achieved.

The V2-CND agents of the invention may also be administered via liposomes, which serve to target the polypeptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations, the V2-CND agents to be delivered are incorporated as part of a liposome, alone or in conjunction with a molecule which binds to, e.g., a receptor prevalent among lymphoid cells, such as monoclonal antibodies which bind to the CD45 antigen, or with other therapeutic, prophylactic or immunogenic compositions. Thus, liposomes either filled or decorated with a desired V2-CND agent of the invention can be directed to the site of lymphoid cells, where the liposomes then deliver the peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) Ann. Rev. Biophys. Bioeng., 9:467, and U.S. Pat. Nos. 4,235,871; 4,501,728; 4,837,028; and 5,019,369.

The V2-CND agents of the invention can also be administered as compositions including a variety of immune-enhancing substances (i.e., substances that enhance an immune response induced in a subject by a V2-CND agent). For example, V2-CND agents can be co-administered with immune stimulating complexes (ISCOMS), which are negatively charged cage-like structure of 30-40 nm in size formed spontaneously on mixing cholesterol and Quil A (saponin). Protective immunity has been generated in a variety of experimental models of infection including toxoplasmosis and Epstein-Barr virus-induced tumors using ISCOMS as the delivery vehicle for antigens (see, e.g., Mowat and Donachie, Immunol. Today, 23:383-385 (1991)). Immunogenic compositions using ISCOMS are comprised of the peptides of the invention encapsulated into ISCOMS for delivery. Additional suitable compositions include, for example, lipopeptides (e.g., Vitiello et al., J. Clin. Invest. 95:341 (1995)), peptide compositions encapsulated in poly (DL-lactide-co-glycolide) ("PLG") microspheres (see, e.g., Eldridge et al., Molec. Immunol. 28:287-94 (1991); Alonsno et al., Vaccine 12:299-306 (1994); Jones et al., Vaccine 13:675-81 (1995)), and multiple antigen peptide systems (MAPs) (see, e.g., Tam, Proc. Natl. Acad. Sci. U.S.A. 85:5409-13 (1988); Tam, J. Immunol. Methods 196:17-32 (1996)). Toxin-targeted delivery technologies, also known as receptor-mediated targeting, such as those of Avant Immunotherapeutics, Inc. (Needham, Mass.) can also be used.

Alternatively, strategies for increasing the effectiveness of an immunogen (e.g., the V2-CND agents) include, for example, strategies whereby an immunogenic polypeptide (e.g., the V2-CND polypeptide or fragments of the polypeptide) can be directly modified to enhance their immunogenicity or physical properties such as stability. For example, cyclization or circularization of a polypeptide can increase the polypeptide's antigenic and immunogenic potency.

In addition, single chain fusion proteins comprising the V2-CND polypeptide covalently linked to a second sequence (e.g., an HIV-1 V3 sequence determinant or a human Ig Fc domain) can also be useful in increasing the efficacy of the V2-CND agents. Fusion can be obtained through chemical synthesis of a synthetic fusion protein, a chemically conjugated fusion of non-synthetic polypeptides, or can be produced by recombinant techniques (e.g., expressed in a cell from a vector containing a nucleic acid encoding the V2-CND polypeptide fused in frame with a nucleic acid encoding the second sequence). The fusion can be direct, or include a flexible linker between to the sequences (e.g., poly-glycine, glycine$_4$-serine). The V2-CND polypeptides can also be covalently linked to "T-helper epitope" sequences, such as for example, the Pan DR (PADRE) T-helper epitope (see, Pamonsinlapatham P. et al. (2004) Scand. J. of Immunol. 59:504-510) at the amino- or carboxy-terminus of the V2-CND polypeptide. The V2-CND can also be oligomerized by covalent fusion to oligomerization/multimerization domain (e.g., leucine zipper coiled-coil motif of GCN4, or the C-terminal oligomerization domain of p53 protein). Such methods are known to those of ordinary skill and are also set forth in the Examples below.

The immunogenicity of the polypeptides of the present invention can also be modulated by coupling to fatty acid moieties to produce lipidated polypeptides. Convenient fatty acid moieties include glycolipid analogs, N-palmityl-S2RS) 2,3-bis-(palmitoyloxy)pmopyl-cysteinyl-serine (PAM3 Cys-Ser), N-palmityl-S-2RS)2,3 bis (palmitoyloxy)-(2RS)-propyl-[R]-cysteine (TPC) or adipalmityl-lysinemoiety. Moreover, the polypeptides may also be conjugated to a lipidated amino acid, such as an octadecyl ester of an aromatic acid, such as tyrosine, including actadecyl-tryrosine (OTH).

The immunogenic agents (e.g., the V2-CND agents), when administered to a subject, also typically include an adjuvant. Adjuvants such as incomplete Freund's adjuvant, aluminum phosphate, aluminum hydroxide, alum, Ribi Adjuvant System (RAS), and Titermax (CytRx Corporation, Los Angeles, Calif.) are examples of materials well known in the art (see, for example, Jennings et al. (1995) ILAR Journal 37:119-125). The proportion of the immunogen (e.g., V2-CND agent) and adjuvant can be varied over a broad range so long as both are present in effective amounts. For example, aluminum hydroxide can be present in an amount of about 0.5% of the immunogen mixture ($Al_2O_3$ basis). On a per-dose basis, the amount of the immunogen can range from about 5 µg to about 100 µµg protein per patient of about 70 kg. A preferable range is from about 20 µµg to about 40 µµg per dose. A suitable dose size is about 0.5 ml. Accordingly, a dose for intramuscular injection, for example, would comprise 0.5 ml containing 20 µg of immunogen in admixture with 0.5% aluminum hydroxide.

Nucleic Acids: The nucleic acids useful for inducing an immune response include at least three components: (1) a V2-CND polypeptide (variant or fragment thereof) coding sequence beginning with a start codon, (2) a mammalian transcriptional promoter operatively linked to the coding sequence for expression of the V2-CND polypeptide, and (3) a mammalian polyadenylation signal operably linked to the coding sequence to terminate transcription driven by the promoter. In this context, a "mammalian" promoter or polyadenylation signal is not necessarily a nucleic acid sequence derived from a mammal. For example, it is known that mammalian promoters and polyadenylation signals can be derived from viruses.

The nucleic acid vector can optionally include additional sequences such as enhancer elements, splicing signals, termination and polyadenylation signals, viral replicons, and bacterial plasmid sequences. Such vectors can be produced by methods known in the art. For example, a nucleic acid encoding the desired V2-CND polypeptide or fragments thereof, can be inserted into various commercially available expression vectors. See, e.g., Invitrogen Catalog, 1998. In addition, vectors specifically constructed for nucleic acid vaccines are described in Yasutomi et al. (1996) J Virol 70:678-681.

The nucleic acids of the invention can be administered to an individual, or inoculated, in the presence of substances that have the capability of promoting nucleic acid uptake or recruiting immune system cells to the site of the inoculation. For example, nucleic acids encapsulated in microparticles have been shown to promote expression of rotaviral proteins from nucleic acid vectors in vivo (U.S. Pat. No. 5,620,896).

A mammal can be inoculated with nucleic acid through any of the routes described herein. The nucleic acids can also be administered, orally, or by particle bombardment using a gene gun. Muscle is a useful tissue for the delivery and expression of V2-CND polypeptide-encoding nucleic acids, because mammals have a proportionately large muscle mass which is conveniently accessed by direct injection through the skin. A comparatively large dose of nucleic acid can be deposited into muscle by multiple and/or repetitive injections. Multiple injections can be used for therapy over extended periods of time.

Administration of nucleic acids by conventional particle bombardment can be used to deliver nucleic acid for expression of a V2-CND polypeptide, variant or fragment thereof, in skin or on a mucosal surface. Particle bombardment can be carried out using commercial devices. For example, the Accell II® (PowderJect® Vaccines, Inc., Middleton, Wis.) particle bombardment device, one of several commercially available "gene guns," can be employed to deliver nucleic acid-coated gold beads. A Helios Gene Gun® (Bio-Rad) can also be used to administer the DNA particles. Information on particle bombardment devices and methods can be found in sources including the following: Yang et al. (1990) Proc Natl Mad Sci USA 87:9568 (1990); Yang et al. (1992) CRC Crit Rev Biotechnol 12:335; Richmond et al. (1997) Virology 230:265-274 (1997); Mustafa et al. (1997) Virology 229:269-278; Livingston et al. (1998) Infect Immun 66:322-329; and Cheng et al. (1993) Proc Natl Acad Sci USA 90:4455.

The V2-CND polypeptide-encoding nucleic acid can be administered to a mucosal surface by a variety of methods including nucleic acid-containing nose-drops, inhalants, suppositories, or microspheres. Alternatively, a nucleic acid vector containing the codon-optimized gene can be encapsulated in poly(lactide-co-glycolide) (PLO) microparticles by a solvent extraction technique, such as the ones described in Jones et al. (1996) Infect Immun 64:489; and Jones et al. (1997) Vaccine 15:814. For example, the nucleic acid is emulsified with PLG dissolved in dichloromethane, and this water-in-oil emulsion is emulsified with aqueous polyvinyl alcohol (an emulsion stabilizer) to form a (water-in-oil)-in-water double emulsion. This double emulsion is added to a large quantity of water to dissipate the dichloromethane, which results in the microdroplets hardening to form microparticles. These microdroplets or microparticles are harvested by centrifugation, washed several times to remove the polyvinyl alcohol and residual solvent, and finally lyophilized. The microparticles containing nucleic acid have a mean diameter of 0.5 μm. To test for nucleic acid content, the microparticles are dissolved in 0.1 M NaOH at 100° C. for 10 minutes. The $A_{260}$ is measured, and the amount of nucleic acid calculated from a standard curve. Incorporation of nucleic acid into microparticles is in the range of 1.76 g to 2.7 g nucleic acid per milligram PLG.

Microparticles containing about 1 to 100 μg of nucleic acid are suspended in about 0.1 to 1 ml of 0.1 M sodium bicarbonate, pH 8.5, and orally administered to mice or humans, e.g., by gavage. Regardless of the route of administration, an adjuvant can be administered before, during, or after administration of the nucleic acid. An adjuvant can increase the uptake of the nucleic acid into the cells, increase the expression of the antigen from the nucleic acid within the cell, induce antigen presenting cells to infiltrate the region of tissue where the antigen is being expressed, or increase the antigen-specific response provided by lymphocytes.

Pharmaceutical Compositions

In another aspect, the present invention provides compositions, e.g., pharmaceutically acceptable compositions. The pharmaceutical compositions of the invention can include a "therapeutically effective amount" or a "prophylactically effective amount" of a V2-CND agent. A "therapeutically effective amount" refers to an amount effective, at dosages and for periods of time necessary, to achieve the desired therapeutic result. A therapeutically effective amount of the V2-CND polypeptides, nucleic acids, compounds and compositions varies according to factors such as the disease state, age, sex, and weight of the individual, and the ability of the V2-CND polypeptides, nucleic acids, compounds and compositions to elicit a desired response in the individual. A therapeutically effective amount is also one in which any toxic or detrimental effects of the pharmaceutical composition is outweighed by the therapeutically beneficial effects.

The ability of a compound to inhibit a measurable parameter can be evaluated in an animal model system predictive of efficacy in humans. Alternatively, this property of a composition can be evaluated by examining the ability of the compound to modulate, such modulation in vitro by assays known to the skilled practitioner.

A "prophylactically effective amount" refers to an amount effective, at dosages and for periods of time necessary, to achieve the desired prophylactic result (e.g., complete prevention of the symptoms of a disease, a delay in onset of the symptoms of a disease, or a lessening in the severity of subsequently developed disease symptoms) against a subsequent challenge by the HIV-1 virus. Typically, since a prophylactic dose is used in subjects prior to or at an earlier stage of disease, the prophylactically effective amount will be less than the therapeutically effective amount.

Pharmaceutically acceptable compositions can include the V2-CND agents described herein, preferably formulated together with a pharmaceutically acceptable carrier. As used herein, "pharmaceutically acceptable carrier" means any and all solvents, dispersion media, isotonic and absorption delaying agents, and the like that are physiologically compatible. Useful carriers for immunogenic compositions (e.g., the V2-CND agents of the invention) are well known in the art, and include, for example, thyroglobulin, albumins such as human serum albumin, tetanus toxoid, polyamino acids such as poly L-lysine, poly L-glutamic acid, influenza, hepatitis B virus core protein, and the like. The compositions and vaccines can contain a physiologically tolerable (i.e., acceptable) diluent such as water, or saline, typically phosphate buffered saline. The carrier can be suitable for intravenous, intramuscular, subcutaneous, parenteral, rectal, spinal or epidermal administration (e.g., by injection or infusion).

The V2-CND agents can be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Useful compositions are in the form of injectable or infusible solutions.

Compositions typically should be sterile and stable under the conditions of manufacture and storage. The composition can be formulated as a solution, microemulsion, dispersion, liposome, or other ordered structure suitable to high concentration of the active ingredient (e.g., V2-CND agents, e.g., the V2-CND polypeptides, nucleic acids, compounds or compositions). Sterile injectable solutions can be prepared by incorporating the active compound (i.e., V2-CND agents) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, both of which yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, V2-CND agents can be orally administered, for example, with an inert diluent or an assimilable edible carrier. The V2-CND polypeptides agents (and other ingredients, if desired) can also be enclosed in a hard or soft shell gelatin capsule, compressed into tablets, or incorporated directly into the subject's diet. For oral administration, the compounds may be incorporated with excipients and used in the form of ingestible tablets, buccal tablets, troches, capsules, elixirs, suspensions, syrups, wafers, and the like. To administer a V2-CND polypeptides, nucleic acids, compounds and compositions of the invention by other than parenteral administration, it may be necessary to coat the V2-CND polypeptides, nucleic acids, compounds and compositions with, or co-administer the V2-CND polypeptides, nucleic acids, compounds and compositions with, a material to prevent its inactivation. Compositions can be administered with medical devices known in the art.

The following examples are meant to illustrate, not limit, the scope of this invention.

EXAMPLES

Example 1

Materials and Methods

Monoclonal Antibodies (mAbs)

The monoclonal antibodies in these examples were obtained as follows. C108g was isolated from a chimpanzee infected with the IIIB strain of HIV-1 and subsequently immunized with isolated MN gp120 (Warder et al. (1994) J. Virol. 68(7):4636-4642). The characteristics of C108g and its epitope were previously described (Warder et al. (1994) J. Virol. 68(7):4636-4642; Vijh-Warrier et al. (1995) Mol. Immunol. 32:1081-1092; Wu et al. (1995) J. Virol. 69(4): 2271-2278; Pinter et al. (2005) J. Virol. 79(11):6909-6917). 10/76b was isolated from a rat immunized with soluble HX1310 gp120 (McKeating et al. (1993) J. Virol. 67(8): 4932-4944) and characteristics of its epitope have been described (Shotton et al. (1995) J. Virol. 69:222-230). 2909 was isolated from an HIV-1-infected human subject by screening for neutralization of HIV-1 pseudotyped with SF162 Env (Gorny et al. (2005) J. Virol. 79(8):5232-5237).

Chimeric and Variant Forms of HIV-1 Env Protein.

The chimeric and variant forms of HIV-1 Env herein were generated as follows. The parental SF162 and JR-FL Envs and chimeric forms of these Envs in which the V1/V2 domains were exchanged (SF(JR V1/V2)) and JR(SF V1/V2)) were previously described (Pinter et al. (2004) J. Virol. 78(10):5205-5215). The various Envs with consensus V3 sequences were generated by introducing the necessary modifications sequentially by Quickchange™ site-directed mutagenesis (Stratagene, Inc., La Jolla, Calif.). The same method was used to prepare the V2 variants used to introduce the C108g and 10/76b epitopes into SF162 Env (Pinter et al. (2005) J. Virol. 79(11):6909-6917) (FIG. 1). These include SF(GKV) in which residues N(K)M at position 167-9 were mutated to G(K)V, SF(NI) in which residues KV at position 160-1 were mutated to NI, SF(NI+GKV) in which both of the above mutations were combined, SF(JR V3) in which the V3 domain corresponded to that of JR-FL, and JR(GK) in which residues DE at position 167-8 were mutated to GK, thereby introducing the C108g and 10/76b epitopes.

Viral Neutralization Assays.

Neutralization activity was determined as previously described (Krachmarov et al. (2001) AIDS Res. Hum Retroviruses. 17(18):1737-1748) with a single-cycle infectivity assay using virions generated from the Env-defective luciferase-expressing pNL4-3.Luc.R$^-$E$^-$ genome (Connor et al. (1995) J. Virol. 206:935-944) pseudotyped with a molecularly cloned HIV-1 Env of interest. In brief, pseudotyped virions were incubated with serial dilutions of mAbs or polyclonal sera from HIV-infected subjects for 1 hour at 37° C., and then added to U87-T4-CCR5 target cells plated out in 96-well plates in RPMI medium containing 10% fetal bovine serum (FBS) and polybrene (10 μg/ml). After 24 hrs, cells were refed with RPMI medium containing 10% FBS and polybrene, followed by an additional 24-48 hrs incubation. Luciferase activity was determined 48-72 hrs post-infection with a microtiter plate luminometer (HARTA Instruments, Inc., Gaithersburg, Md.), using assay reagents from Promega (Madison, Wis.). $ND_{50}$ values reported were determined by interpolation from neutralization curves and are averages of at least three independent assays.

Example 2

Mapping the Critical Determinants of 2909 Reactivity to the V2 Domain

The V2 and V3 domain determinants required for 2909 mAb binding were mapped by examining the neutralizing activity of this mAb against a series of SF162 mutants and variants bearing changes in both the of these domains. As previously reported, 2909 possessed extremely potent neutralizing activity for SF162, with an $ND_{50}$ in the low pg/ml range (0.000058 μg/ml). Substituting the V3 domain of SF162 with that of the Glade B consensus sequence (identical to that of the JR-FL isolate) resulted in a significant attenuation in potency, with an almost 900-fold increase in $ND_{50}$. The SF162 sequence differs from that of the clade B consensus at three positions, substitution of T for H at the highly polymorphic position 13, A for T at position 22 and D for E at position 25. An analysis of the effect of single residue substitution at these three positions on attenuation of neutralization activity of 2909 showed that the three changes contributed to this effect to different extents. The greatest effect (46-fold) was due to the A22T substitution, while the T13H substitution resulted in an 8.3-fold increase and the D25E a 2.3-fold increase in $ND_{50}$. The overall attenuation matches very closely to the product of the three individual effects, and thus the effects of the individual substitutions on infectivity appeared to be multiplicative.

2909 also possessed considerable neutralizing activity for a number of V3 variants that corresponded to the consensus sequences of six different HIV-1 sub-types sequences, also expressed in the SF162 backbone (Table 1). Three variants corresponding to the consensus sequences for subtypes C, A1 and F required ~100-fold higher 2909 concentrations than SF162 itself to achieve 50% neutralization. Interestingly, these V3 variants were ~10-fold more sensitive to 2909 than the Glade B V3 consensus sequence. Other variants corresponding to consensus sequences for sub-types CFF02_AG and Glade H also retained sensitivity to 2909, but were neutralized less potently than the Glade B consensus sequence, while the highly variant CRF01_AE consensus sequence was completely insensitive to neutralization by this mAb.

TABLE 1

Effect of V3 sequence variation on
neutralization sensitivity of 2909
for chimeric SF162

| V3 regions | | $ND_{50}$ [a] | $ND_{50}$ ratio [b] |
|---|---|---|---|
| SF162 | CTRINNNTRKSITIGPGRAFYATGDIIGDIRQAHC | 0.000058 | — |
| clade C cons | ------------R----QT---------------- | 0.0048 | 83 |
| clade A1 cons | ------------R----Q----------------- | 0.0064 | 110 |
| clade F cons | ------------H----Q------E------K--- | 0.0076 | 131 |
| CRF02_AG | -----------VR----QT---------------- | 0.037 | 637 |
| clade B cons | ------------H--------T--E---------- | 0.051 | 879 |
| clade H cons | ------------HL---Q----------------- | 0.17 | 2,931 |
| CRF01_AE cons | ----S----T-------QV--R---------K-Y- | >20 | >344,000 |

[a] $ND_{50}$s reported are in µg/ml, and are averages of at least three independent measurements
[b] Indicates the fold increase in $ND_{50}$ for the variant V3s over the SF162 sequence.
SF162 amino acid sequence is SEQ ID NO: 18; clade C cons. amino acid sequence is SEQ ID NO: 19; Clade A1 cons. amino acid sequence is SEQ ID NO: 20; clade F cons. amino acid sequence is SEQ ID NO: 21; CRF02_AG amino acid sequence is SEQ ID NO: 22; clade B cons. amino acid sequence is SEQ ID NO: 23; clade H cons. amino acid sequence is SEQ ID NO: 24; and SRF01_AE cons. amino acid sequence is SEQ ID NO: 25.

While these results confirmed a role for the V3 domain in expression of the 2909 epitope and in the extreme sensitivity of SF162 Env to this mAb, they also demonstrated a considerable tolerance of 2909 reactivity for V3 sequence variation. The neutralizing efficacy for 2909 for many of the sequences with attenuated reactivity remained in the low ng/ml range, similar in potency to the best of the standard anti-V3 mAbs and considerably more potent than the so-called "broadly-neutralizing" antibodies for these viruses. Thus, while specific features of the SF162 V3 sequence are required for the extreme potency of 2909 for viruses with SF162 Env, 2909 retained sufficient affinity for a number of SF162 Env variants expressing V3 domains corresponding to consensus sequences of multiple viral subtypes to allow 50% neutralization at sub-picomolar concentrations of the mAb.

Example 3

Mapping the V2 Determinants of 2909 Reactivity

Figure 2B:
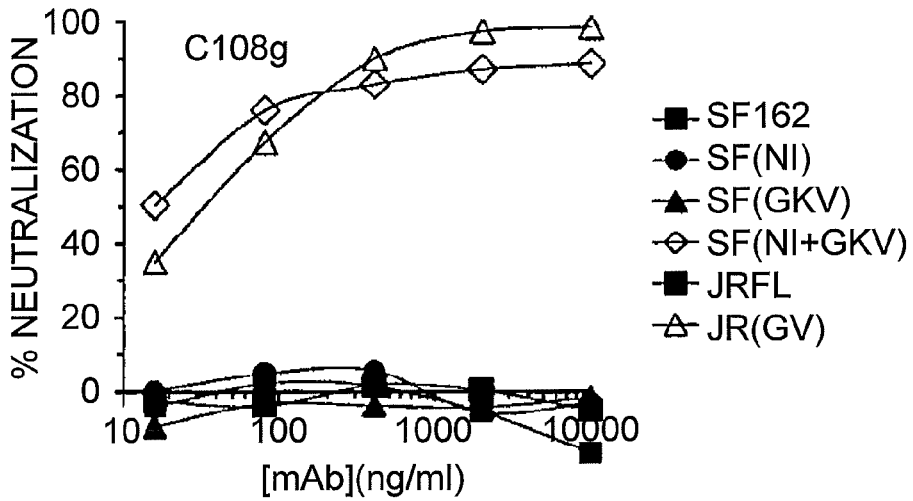
FIG. 2B: C108g mAb; Wild-type SF162 gp120 (closed squares), SF162 gp120 with NI at positions 161 and 162 (closed circles), SF162 with GKV at positions 167-169 (closed triangles), SF162 with said GKV at positions 167-169 and NI at positions 161 and 162 (open diamonds), and Wild-type JR-FL gp120 (closed squares), and JR-FL gp120 with GV at positions 167 and 168 (open triangles). Lower Panel, 10/76b mAb; Wild-type SF162 gp120 (closed squares), SF162 gp120 with NI at positions 161 and 162 (closed circles), SF162 with GKV at positions 167-169 (closed circles), SF162 with said GKV and NI at positions 161 and 162 (open diamonds), and Wild-type JR-FL gp120 (open triangles), and JR-FL gp120 with GV at positions 167 and 168 (open triangles). Note the expanded range of antibody concentration for the 2909 titration. Antibody concentrations are presented as ng/ml.
Figure 2C:
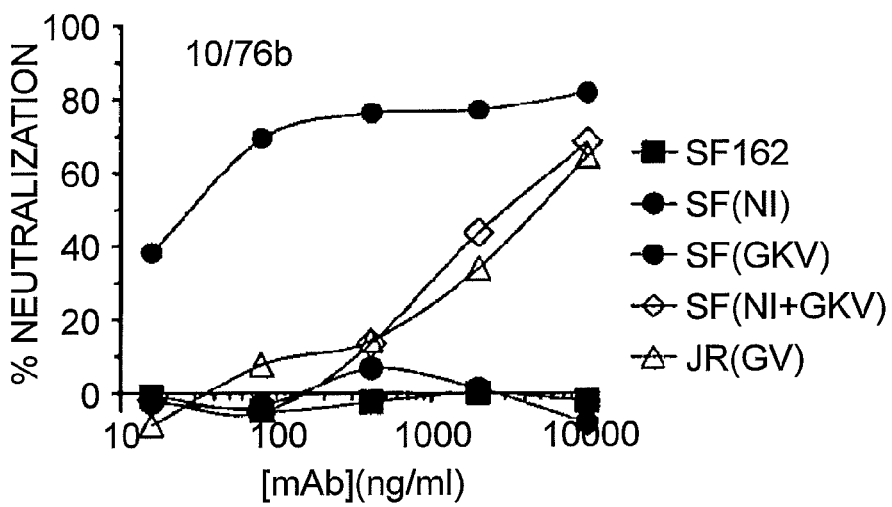

To map determinants in the V2 domain required for 2909 reactivity, the neutralizing activity of 2909 for a series of V1/V2 mutants and variants was examined. These included a chimeric Env protein in which the V1/V2 domain of SF162 Env were replaced by that of JR-FL Env (which is not recognized by 2909), and V2 domain mutants used to introduce the C108g and 10/76b epitopes into SF162 Env (FIG. 1). Substitution of the complete SF162 V1/V2 domain by the JR-FL sequence resulted in complete loss of reactivity, confirming a critical role for the V1/V2 domain in the 2909 epitope (Table 2). Consistent with this, substitution of the SF162 V1/V2 domain into JR-FL Env resulted in neutralization sensitivity similar to that of the SF162 chimera with the JR-FL V3 domain, indicating that all of the determinants for the selective reactivity of 2909 for SF162 over JR-FL were localized to the V1/V2 and V3 domains. Analysis of V2 mutants that were used to introduce the C108g and 10/76b epitopes into SF162 Env showed a reciprocal relationship between these epitopes and the 2909 epitope. An essential component of both the C108g and 10/76b epitopes is the presence of residues GKV at position 167-169; for SF162 Env the corresponding residues are NKM (FIG. 1). Substitution of the G and V into SF162 resulted in a >1,000-fold increase in 2909 concentration required for 50% neutralization. An additional component required for expression of the C108g epitope is the N-linked glycosylation site at position 160. Introducing this site into SF162 by substituting the KV present at positions 160-1 with NI, either by itself or in conjunction with the G-V substitution, resulted in the complete loss of 2909 reactivity (FIG. 2. Table 2). Thus, both of the V2 regions that are required for C108g reactivity are also major determinants of expression of the 2909 epitope.

TABLE 2

$ND_{50}$s (µg/ml) for three mAbs dependent on
sequences in the V2 domain.

| Env | $ND_{50}$ C108g | $ND_{50}$ 10/76b | $ND_{50}$ 2909 |
|---|---|---|---|
| SF162 | >>10 | >>10 | 0.00049 |
| SF(JR V1/V2) | >>10 | >>10 | >>10 |
| JR(SF V1/V2) | >>10 | >>10 | 0.065 |
| SF(GKV) | >>10 | 0.032 | 0.54 |
| SF(NI) | >>10 | >>10 | >>10 |
| SF(NI + GKV) | 0.016 | 3.3 | >>10 |
| SF(JR V3) | >>10 | >>10 | 0.145 |
| JR(GKV) | 0.037 | 6.0 | >>10 |
| JR-FL | >>10 | >>10 | >>10 |

Example 4

Generating an Enhanced Version of the 2909
Epitope in the JR-FL Env

Figure 4:
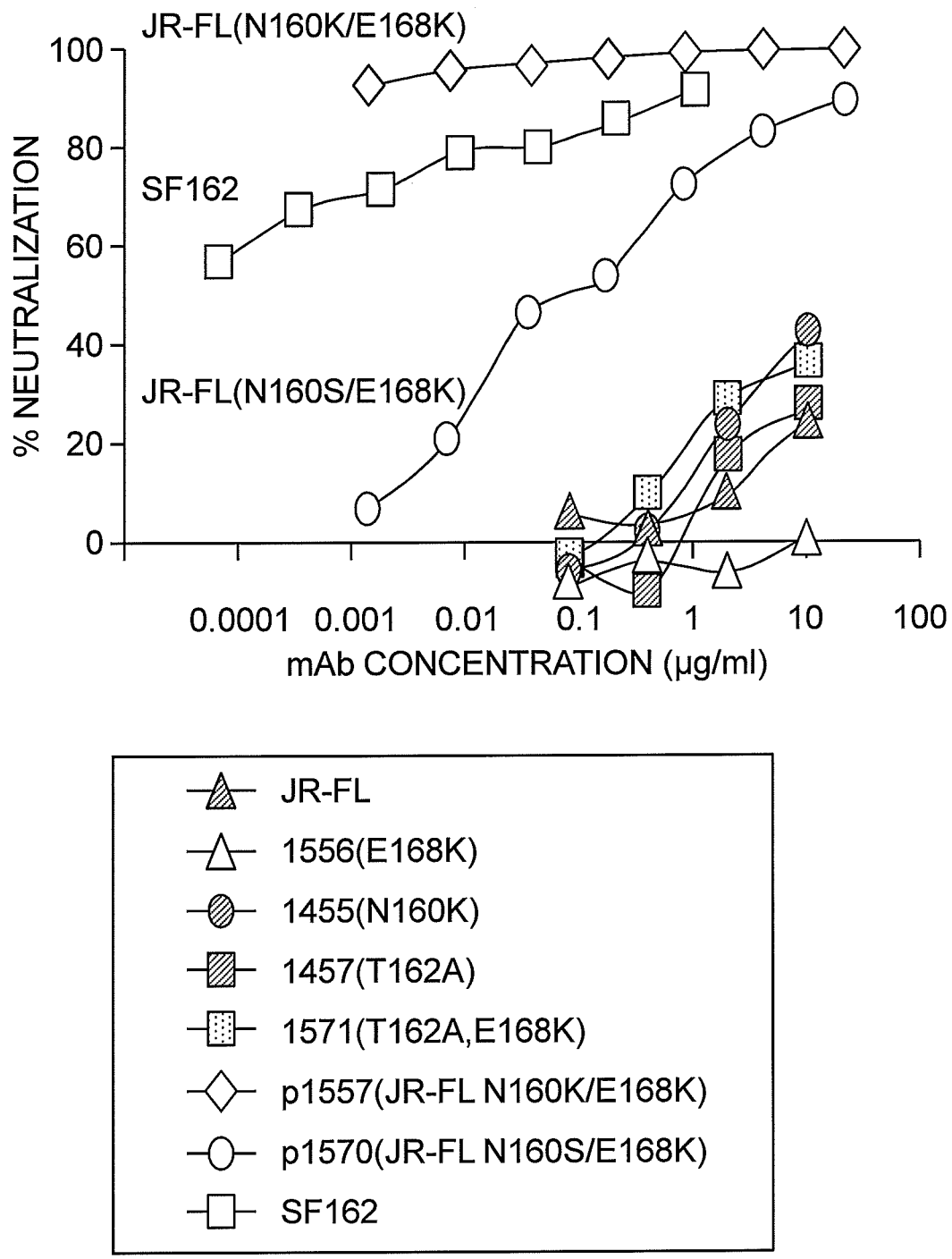
FIG. 4 is a line graph depicting the neutralization curves of several JR-FL mutants by mAb 2909. This shows the enhanced sensitivity of the JRFL(KK) mutant to neutralization by 2909. Antibody concentrations are presented as µg/ml.

Additional information about the 2909 epitope was obtained by an analysis of mutants of JR-FL Env that had additional modifications in the V2 region defined by the above studies (FIGS. 3 and 4). The parental JR-FL Env was completely resistant to 2909. Whereas the SF162 sequence at position 167-9 was NKM, the corresponding sequence in JR-FL was DEV. Changing the E at position 168 to K did not by itself result in 2909 reactivity, and neither did introducing a K at position 160. However, combining K168 with changes at position 160 did introduce the 2909 epitope. The double mutant in which N160 was changed to S was neutralized by 2909, although not as potently as the SF162 Env (FIG. 4). However, the JR-FL mutant containing both the K160 and K168 mutations was considerably more sensitive to neutralization by 2909 than SF162 itself. Particularly striking was the ability of 2909 to achieve >99% neutralization of the latter mutant at concentrations as low as 20 ng/ml, despite the fact that this Env had a sub-optimal V3 sequence. Eliminating the glycan at position 160 by changing T162 to A did not result in neutralization by 2909, suggesting that simply removal of the glycan at position 160 was not sufficient for 2909 reactivity, and that the presence of lysine residues at both positions 160 and 168 significantly enhanced the potency of the epitope for 2909.

Figure 5:
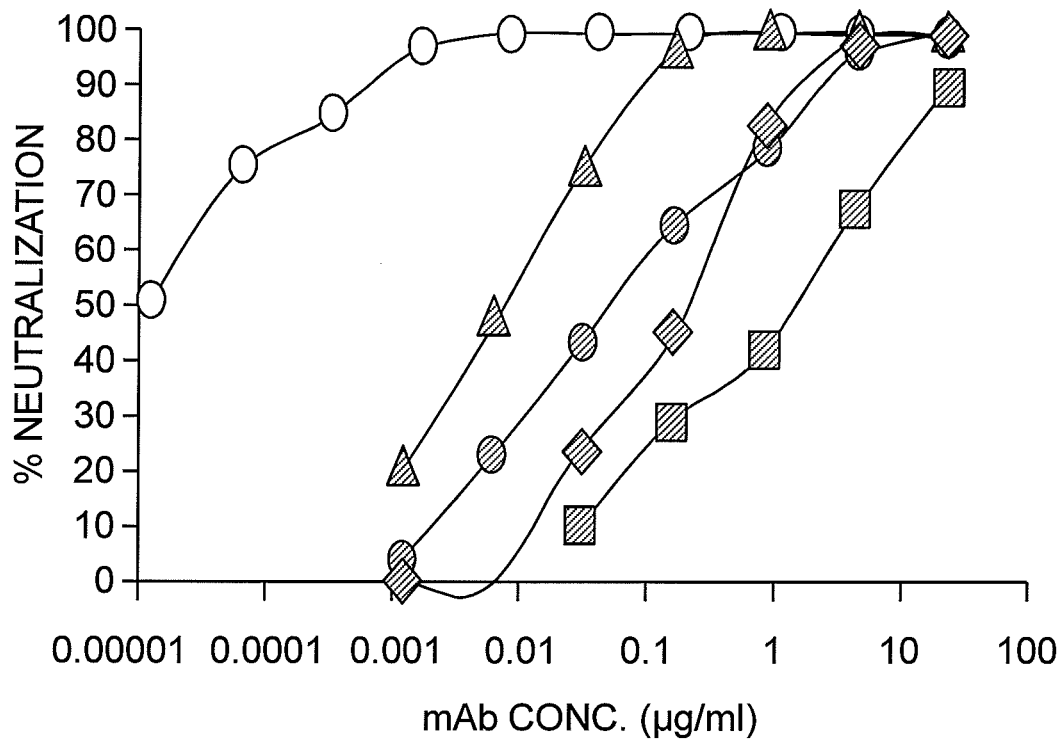
FIG. 5 is a line graph depicting the neutralization curves of several HIV-1 virus JR-FL (N160K/E168K) variants with the 2909 mAb, and several other standard HIV-1 neutralizing antibodies. Representative neutralization curves of chimeric JR-FL Env to the 2909 antibody and several other standard HIV neutralizing antibodies. Antibody concentrations are presented as □g/ml.

A comparison of the sensitivity of the N160K/E168K JR-FL mutant to neutralization by standard mAbs further highlighted the remarkable potency of 2909 (FIG. 5). 2909 neutralized this virus with an $ND_{50}$ of <0.04 ng/ml; this was ~20-fold more potent than IgG-b12, >140-fold more potent than 2F5, >500-fold more potent than 2G12, and ~4,000-fold more potent than a pool of potent V3-specific mAbs. The 160K/168K JR-FL mutant was about 20-fold more sensitive to these anti-V3 mAbs than the parental JR-FL, consistent with a modest masking effect of the 160 glycan on the V3 domain. However, the relatively small increase in sensitivity to anti-V3 mAbs and the typical sensitivity of this mutant to neutralization by the other mAbs indicates that the changes in V2 did not introduce a global neutralization sensitivity into this Env. These results provide further support for the exceptional neutralizing potency of 2909 and the exquisite sensitivity of this target site in V2 to neutralization.

The clade B consensus sequence of the V2 region contains a K at position 168, and otherwise is identical to the JR-FL sequence. Thus, the optimal 2909, sequence differs from the consensus sequence by only a single amino acid (K160). Interestingly, the C108g epitope contains the consensus sequence at positions 160-2 (NIT), and also differs from the consensus sequence by only a single residue, at position 167 (D for G). This shows that despite the type-specificity of these mAbs, the sequences of both epitopes are actually highly related to the consensus sequence, differing only by single substitutions at different positions. The potent recognition by 2909 of the K160/K168 JR-FL mutant containing consensus residues DKV at position 167-9 shows that this consensus sequence is inherently immunogenic, providing support for the likelihood that consensus forms of the C108g epitope would also be immunogenic.

What is claimed is:

1. An antibody which binds a polypeptide comprising-an amino acid sequence EIKNC SFNXT TXXRD KXXXX YXLFY XLDXV (SEQ ID NO:1) or a fragment thereof wherein the amino acid sequence includes KQKV (SEQ ID NO:3), KQKE (SEQ ID NO:4), KKKE (SEQ ID NO:26), KKKV (SEQ ID NO:27), KRQE (SEQ ID NO:28), KRKV (SEQ ID NO:29), KKQV (SEQ ID NO:30) or KKQE (SEQ ID NO:31) at amino acid positions 17-20, and wherein the X at position 9 of SEQ ID NO:1 is M or I;

the X at position 12 of SEQ ID NO:1 is S, E, G, or N;

the X at position 13 of SEQ ID NO:1 is L, I, or M;

the X at position 22 of SEQ ID NO:1 is S or A;

the X at position 26 of SEQ ID NO:1 is K or R; and the X at position 29 of SEQ ID NO:1 is I or V;

wherein said antibody neutralizes more than one HIV-1strain.

2. The antibody of claim 1 wherein the polypeptide is flanked at either end, or both ends, by a heterologous amino acid sequence.

3. The antibody of claim 1, wherein the polypeptide is glycosylated.

4. A method of potently neutralizing the activity of multiple HIV-1 isolates, the method comprising contacting a cell or an HIV-1 virus with the antibody of claim 1. The claim was amended to correct an obvious grammatical mistake.

* * * * *

UNITED STATES PATENT AND TRADEMARK OFFICE
CERTIFICATE OF CORRECTION

PATENT NO. : 9,796,773 B2  
APPLICATION NO. : 14/463040  
DATED : October 24, 2017  
INVENTOR(S) : Abraham Pinter Page 1 of 1

It is certified that error appears in the above-identified patent and that said Letters Patent is hereby corrected as shown below:

In the Claims

At Column 38, Line 62, delete "1strain"

At Column 38, Line 62, add -- 1 strain --

At Column 39, Lines 3-5, delete "The claim was amended to correct an obvious grammatical mistake."

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*